(12) United States Patent
Møller et al.

(10) Patent No.: US 8,632,509 B2
(45) Date of Patent: Jan. 21, 2014

(54) INJECTION DEVICE WITH ELECTRONIC DETECTING MEANS

(75) Inventors: Claus Schmidt Møller, Fredensborg (DK); Bo Kvolsbjerg, Helsingør (DK)

(73) Assignee: Novo Nordisk A/S, Bagsvaerd (DK)

( * ) Notice: Subject to any disclaimer, the term of this patent is extended or adjusted under 35 U.S.C. 154(b) by 124 days.

(21) Appl. No.: 13/245,381

(22) Filed: Sep. 26, 2011

(65) Prior Publication Data

US 2012/0078194 A1 Mar. 29, 2012

Related U.S. Application Data

(63) Continuation of application No. 12/442,168, filed as application No. PCT/EP2007/060331 on Sep. 28, 2007, now Pat. No. 8,052,655.

(60) Provisional application No. 60/851,523, filed on Oct. 13, 2006.

(30) Foreign Application Priority Data

Sep. 29, 2006 (EP) .................................... 06020547

(51) Int. Cl.
*A61M 5/00* (2006.01)
(52) U.S. Cl.
USPC ........................................................ 604/246
(58) Field of Classification Search
USPC .......................................... 604/121, 131, 246
See application file for complete search history.

(56) References Cited

U.S. PATENT DOCUMENTS

| | | | |
|---|---|---|---|
| 3,944,843 A | 3/1976 | Vaz Martins |
| 4,515,584 A | 5/1985 | Abe et al. |
| 4,634,431 A | 1/1987 | Whitney et al. |
| 4,812,724 A | 3/1989 | Langer et al. |
| 4,838,860 A | 6/1989 | Groshong et al. |
| 4,871,351 A | 10/1989 | Feingold |
| 4,898,578 A | 2/1990 | Rubalcaba |
| 4,950,246 A | 8/1990 | Muller |
| 5,135,485 A | 8/1992 | Cohen et al. |

(Continued)

FOREIGN PATENT DOCUMENTS

| | | |
|---|---|---|
| CA | 2359375 | 7/2000 |
| DE | 3236374 | 4/1984 |

(Continued)

OTHER PUBLICATIONS

Beckmann, Sensors, Memory, Circuits, Polyapply Newsletter, vol. 1(3) (2006).

(Continued)

*Primary Examiner* — Nicholas Lucchesi
*Assistant Examiner* — Diva K Chander
(74) *Attorney, Agent, or Firm* — Wesley A. Nicolas; Marc A. Began; Reza Green

(57) ABSTRACT

An injection device for injecting a dose of drug, e.g. insulin for diabetes treatment, in which energy is stored in a spring member during dose setting. The stored energy is released and used for driving an injection mechanism during injection of a previously set dose. The injection device further comprises means for electronically detecting the amount of a set dose and/or means for electronically detecting the amount of an injected dose. The electronic detecting means allows storage and/or logging of data relating to injections performed using the injection device.

20 Claims, 16 Drawing Sheets

(56) References Cited

U.S. PATENT DOCUMENTS

| | | | |
|---|---|---|---|
| 5,163,904 A | 11/1992 | Lampropoulos et al. | |
| 5,221,268 A | 6/1993 | Barton et al. | |
| 5,320,609 A * | 6/1994 | Haber et al. | 604/135 |
| 5,536,249 A | 7/1996 | Castellano et al. | |
| 5,593,390 A | 1/1997 | Castellano et al. | |
| 5,628,309 A | 5/1997 | Brown | |
| 5,662,612 A | 9/1997 | Niehoff | |
| 5,681,285 A | 10/1997 | Ford et al. | |
| 5,720,733 A | 2/1998 | Brown | |
| 5,728,074 A * | 3/1998 | Castellano et al. | 604/207 |
| 5,741,211 A | 4/1998 | Renirie et al. | |
| 5,820,602 A * | 10/1998 | Kovelman et al. | 604/187 |
| 5,879,360 A | 3/1999 | Crankshaw | |
| 5,879,630 A * | 3/1999 | Lescouzeres et al. | 422/82.02 |
| 5,928,201 A * | 7/1999 | Poulsen et al. | 604/208 |
| 5,933,671 A | 8/1999 | Stephany et al. | |
| 5,971,963 A | 10/1999 | Choi | |
| 5,989,221 A | 11/1999 | Hjertman | |
| 5,998,989 A | 12/1999 | Lohberg | |
| 6,019,745 A | 2/2000 | Gray | |
| 6,110,148 A | 8/2000 | Brown et al. | |
| 6,161,364 A | 12/2000 | Kolberg | |
| 6,268,722 B1 | 7/2001 | Kogure et al. | |
| 6,340,357 B1 | 1/2002 | Poulsen et al. | |
| 6,391,005 B1 | 5/2002 | Lum et al. | |
| 6,547,755 B1 | 4/2003 | Lippe et al. | |
| 6,585,698 B1 * | 7/2003 | Packman et al. | 604/207 |
| 6,673,033 B1 | 1/2004 | Sciulli et al. | |
| 7,080,936 B1 | 7/2006 | Simpson | |
| 7,195,609 B2 | 3/2007 | Huegli | |
| 7,195,616 B2 * | 3/2007 | Diller et al. | 604/224 |
| 7,704,238 B2 * | 4/2010 | Diller et al. | 604/224 |
| 2002/0002326 A1 | 1/2002 | Causey, III et al. | |
| 2002/0020654 A1 | 2/2002 | Eilersen | |
| 2003/0009133 A1 | 1/2003 | Ramey | |
| 2003/0073954 A1 | 4/2003 | Moberg et al. | |
| 2003/0114800 A1 | 6/2003 | Veasey et al. | |
| 2003/0216663 A1 | 11/2003 | Willuhn et al. | |
| 2003/0233075 A1 | 12/2003 | Huegli | |
| 2004/0010204 A1 | 1/2004 | Weber et al. | |
| 2004/0024361 A1 | 2/2004 | Fago | |
| 2004/0051368 A1 | 3/2004 | Caputo et al. | |
| 2004/0158304 A1 | 8/2004 | Cory et al. | |
| 2004/0171983 A1 | 9/2004 | Sparks et al. | |
| 2004/0207385 A1 | 10/2004 | Gafner et al. | |
| 2004/0210199 A1 | 10/2004 | Atterbury et al. | |
| 2004/0230157 A1 | 11/2004 | Perry et al. | |
| 2004/0267207 A1 | 12/2004 | Veasey et al. | |

FOREIGN PATENT DOCUMENTS

| | | |
|---|---|---|
| DE | 3923079 | 1/1991 |
| DE | 19503230 | 8/1996 |
| DE | 10201875 | 5/2003 |
| DE | 102004046003 | 3/2006 |
| DK | 200100240 | 2/2001 |
| DK | 2005/00116 | 6/2005 |
| EP | 017318 | 10/1980 |
| EP | 338806 | 10/1989 |
| EP | 387854 | 9/1990 |
| EP | 422482 | 4/1991 |
| EP | 454331 | 10/1991 |
| EP | 615762 | 9/1994 |
| EP | 1074273 | 2/2001 |
| EP | 1095668 | 2/2001 |
| EP | 1095668 A1 | 5/2001 |
| EP | 1557163 | 7/2005 |
| EP | 1557189 | 7/2005 |
| EP | 1723977 | 11/2006 |
| EP | 1728529 | 12/2006 |
| EP | 1782853 | 5/2007 |
| EP | 2000161 | 12/2008 |
| FR | 2622457 | 5/1989 |
| FR | 2740345 | 4/1997 |
| GB | 2153445 | 8/1985 |
| GB | 2229497 | 9/1990 |
| GB | 2309644 | 8/1997 |
| IN | 165367 | 3/1986 |
| JP | 56-163486 | 12/1981 |
| JP | 01-100495 | 4/1989 |
| JP | 02-126184 | 5/1990 |
| JP | 02-182267 | 7/1990 |
| JP | 7-502678 | 3/1995 |
| JP | 09166474 | 6/1997 |
| JP | 3017167 | 11/1999 |
| JP | 2004-535590 A | 11/2004 |
| JP | 2006250582 | 9/2006 |
| WO | WO 85/02256 | 5/1985 |
| WO | WO90/09202 | 8/1990 |
| WO | WO93/01573 | 1/1993 |
| WO | WO95/24233 | 9/1995 |
| WO | WO97/30742 | 8/1997 |
| WO | WO99/07425 | 2/1999 |
| WO | WO99/15214 | 4/1999 |
| WO | WO99/65548 | 12/1999 |
| WO | WO0037129 | 6/2000 |
| WO | WO01/26710 | 4/2001 |
| WO | WO02/05876 | 1/2002 |
| WO | WO0224257 | 3/2002 |
| WO | WO02/053214 | 7/2002 |
| WO | WO02/064196 | 8/2002 |
| WO | WO02092153 | 11/2002 |
| WO | WO03/057283 | 7/2003 |
| WO | WO03/063680 | 8/2003 |
| WO | WO97/33638 | 9/2003 |
| WO | WO03/099357 | 12/2003 |
| WO | WO2004/028598 | 4/2004 |
| WO | WO2004/080306 | 9/2004 |
| WO | WO2004/084795 | 10/2004 |
| WO | WO2004/095379 | 11/2004 |
| WO | WO2005/089835 | 9/2005 |
| WO | WO2006/039930 | 4/2006 |
| WO | 2006/045425 A1 | 5/2006 |
| WO | 2006/045525 A1 | 5/2006 |
| WO | WO2006/045425 | 5/2006 |
| WO | WO2006/045525 | 5/2006 |
| WO | WO2006/045529 | 5/2006 |
| WO | 2006/076921 A1 | 7/2006 |
| WO | WO2006/069454 | 7/2006 |
| WO | WO2006/076921 | 7/2006 |
| WO | WO2006/116997 | 11/2006 |
| WO | WO2006/128794 | 12/2006 |
| WO | WO2007/030957 | 3/2007 |
| WO | WO2007/041843 | 4/2007 |
| WO | WO2007/107558 | 9/2007 |
| WO | WO2007/107561 | 9/2007 |
| WO | WO2007/134954 | 11/2007 |
| WO | WO2008/037801 | 4/2008 |
| WO | WO2008057223 | 5/2008 |

OTHER PUBLICATIONS

Trankler, Hans-Rolf, R. Oldenbourg, Verlag, Munchen, Wien.
English Abstract of DE10201875.
English Abstract of DE102004046003.
English Abstract of DE19503230.
English Abstract of DE3923079.
English Abstract of DE3236374.
English Abstract of EP387854.
English Abstract of EP422482.
English Abstract of FR2622457.
English Abstract of FR2740345.
English Abstract of IN165367.
Machine Translation of JP09166474.
English Abstract of JP2006250582.
English Abstract of JP02-126184.
English Abstract of JP56-163486.
English Abstract of JP3017167.
English Abstract of JP01-100495.
English Abstract of JP02-182267.
Common Insulin Injection Challenges: http://www.bd.com/us/diabetes/page.aspx?cat=7001&id=7265.

(56) References Cited

OTHER PUBLICATIONS

Gnanalingham, M.G. et al., Accuracy and Reproducibility of Low Dose Insulin Administration Using Pen-Injectors and Syringes, Downloaded From adc.bmj.com on January 9, 2008.

Annersten, M. et al., Insulin Pens Dribble From the Tip of the Needle After Injection, Practical Diabetes Int., vol. 17(4), pp. 109-111 (2000).

* cited by examiner

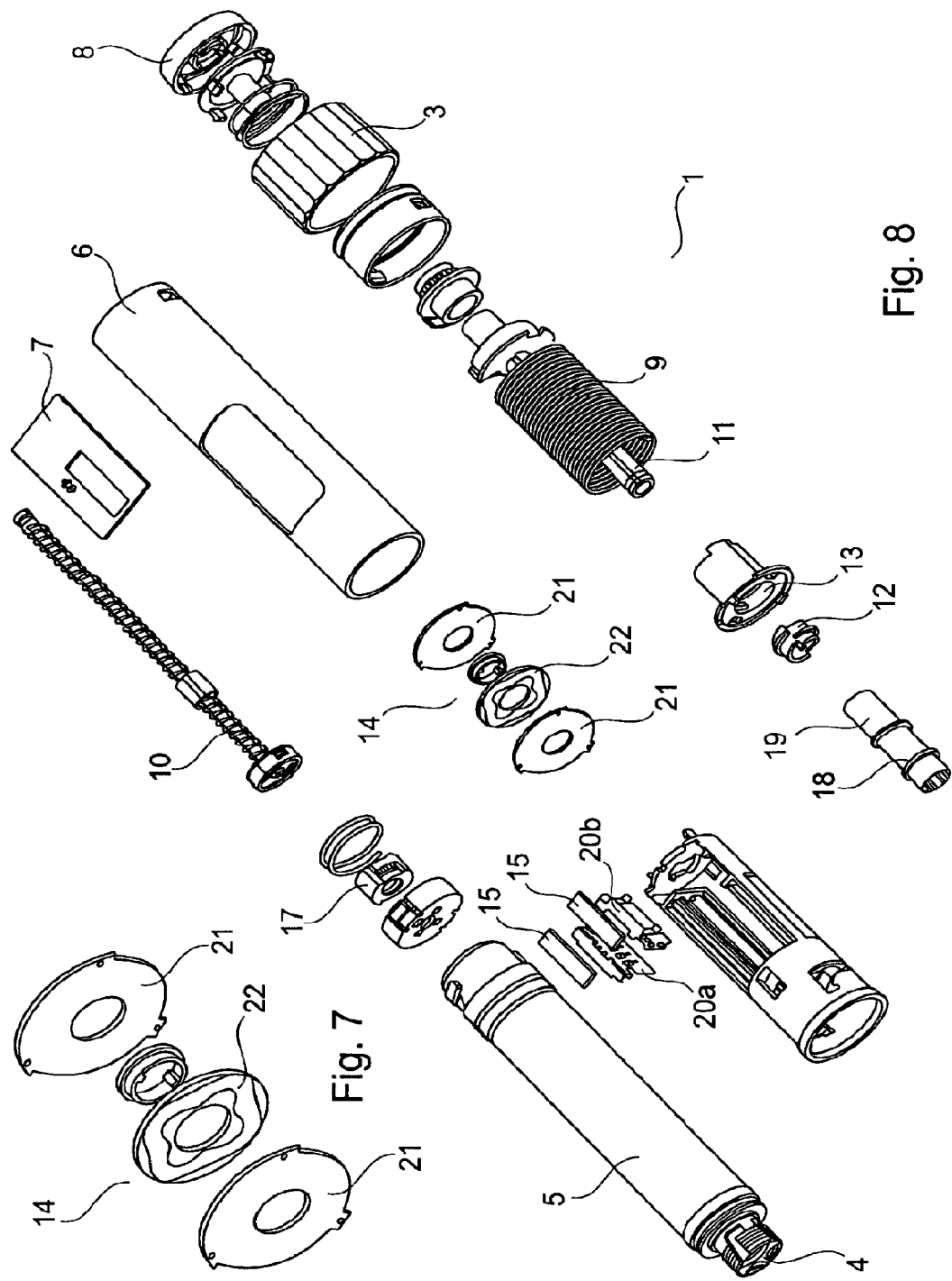

INJECTION DEVICE WITH ELECTRONIC DETECTING MEANS

CROSS-REFERENCE TO RELATED APPLICATIONS

This application is a continuation of U.S. Ser. No. 12/442,168 (Notice of Allowance Received) filed Mar. 20, 2009, which is a 35 U.S.C. §371 national stage application of International Patent Application PCT/EP2007/060331 (published as WO 2008/037801), filed Sep. 28, 2007, which claimed priority of European Patent Application 06020547.3, filed Sep. 29, 2006; this application further claims priority under 35 U.S.C. §119 of U.S. Provisional Application 60/851,523, filed Oct. 13, 2006; the contents of all the above-named applications are incorporated herein by reference.

FIELD OF THE INVENTION

The present invention relates to an injection device having a dose setting mechanism, the operation of which causes energy to be stored in a spring member, i.e. a so-called 'auto injection device'. More particularly, the present invention relates to an injection device as described above, and comprising electronic detection means for detecting the amount of a set dose and/or the amount of an injected dose.

BACKGROUND OF THE INVENTION

Various injection devices have been described, which comprise energy storing means, such as a spring member, in which energy is stored during dose setting. Subsequently, during injection of a previously set dose, energy stored in the energy storing means is released and used for driving an amount of drug corresponding to the previously set dose out of the injection device.

Examples of such injection devices are shown in WO 2006/045528 and in WO 2006/045529. The injection devices disclosed in WO 2006/045528 and in WO 2006/034429 both comprise mechanical means, in the form of a dose indicator barrel, for detecting and displaying the amount of a set dose. During injection, the dose indicator barrel returns to its initial position, and it is thereby also capable of indicating the amount of an injected dose.

In some cases it may be desirable to store and/or log data relating to the injections performed using the injection device, e.g. in order to be able to compare such data. However, it is undesirable if this results in an increased size of the injection device.

Furthermore, in some cases it is desirable to provide an electronic display at an exterior part of the housing of the injection device for displaying various relevant parameters, such as set dose, injected dose, time lapsed since last dose was injected, kind of medicament contained in the device, etc. At the same time, it is desirable to be able to monitor relevant parts of the injection device, in particular to monitor movements of such relevant parts, in order to obtain desired information to be displayed at the display.

SUMMARY OF THE INVENTION

It is, thus, an object of the invention to provide an injection device comprising energy storing means as described above, and in which the accuracy of detecting the amount of a set dose and/or the amount of an injected dose is improved as compared to similar prior art injection devices.

It is a further object of the invention to provide an injection device which provides the possibility of storing and/or logging data relating to injections performed using the injection device without increasing the size of the injection device as compared to similar prior art injection devices.

According to the invention the above and other objects are fulfilled by providing an injection device for injecting a dose of drug, the injection device comprising:

a dose setting mechanism being operable to set a desired dose, operation of said dose setting mechanism causing energy to be stored in a spring member, an injection mechanism comprising a piston rod adapted to cooperate with a piston positioned in a cartridge containing a drug to be delivered in order to cause a set dose to be delivered from the cartridge via the injection device, said injection mechanism being driven by releasing energy previously stored in said spring member during dose setting, means for electronically detecting the amount of a set dose and/or means for electronically detecting the amount of an injected dose, and electronic display means for displaying a set dose and/or an injected dose to a user.

The injection device according to the present invention is particularly suitable for repetitive self injections, such as injections of growth hormone, or of insulin for treatment of diabetes, because the injection device can be operated in an easy and intuitive manner, and it is therefore not necessary that the person operating the injection device is a medical staff member or similar. The injection device may advantageously have an elongated shape, i.e. the injection device may be a 'pen-like' injection device.

The dose setting mechanism is operable to set a desired dose. Thus, the dose setting mechanism is a mechanism which the user operates when he or she wishes to set a dose to be injected. The dose setting mechanism may be rotationally operable, i.e. it may comprise a member which the user must rotate in order to set a dose, e.g. in the form of a dose knob. Alternatively, the dose setting mechanism may be substantially linearly operable. In this case the dose setting mechanism comprises a member which the user must pull or push in a substantially linear movement in order to set a desired dose.

Operation of the dose setting member causes energy to be stored in a spring member. This may, e.g., be achieved by compressing a compressible spring member, by tensioning a torsion spring, or in any other suitable manner. The important feature is that the spring member is capable of storing energy during dose setting and of releasing the stored energy during injection of a set dose. Thereby the stored energy causes the set dose to be injected, i.e. it is not necessary for the user to apply further force or movement to the injection device during injection in order to cause a set dose to be injected. This is an advantage because it ensures a very uniform delivery of the drug. It is also possible for the user to keep the injection device more still during injection because it is not necessary to move the fingers in order to cause the dose to be injected. Furthermore, it is possible to control the injection speed, and the medication is thereby allowed to distribute in a more appropriate manner. Keeping the injection device still and controlling the injection speed both result in reduced pain experienced by the user during injection. Furthermore, this is an advantage in the case that the user has low dexterity or impaired finger strength, because in this case it may be difficult for the user to apply the necessary force to the injection device in order to cause the set dose to be injected, thereby introducing the risk that an insufficient amount of drug is injected. This risk is eliminated in the injection device according to the present invention.

The injection device comprises means for electronically detecting the amount of a set dose and/or means for electronically detecting the amount of an injected dose. Thus, the injection device is capable of keeping track of the amount of a set dose, the amount of an injected dose, or the amount of a set dose as well as the amount of an injected dose. Furthermore, the detection is performed electronically rather than mechanically, such as by means of a helically moving scale drum. As a consequence, the detection may be performed very accurately. Furthermore, since there is no requirement of the presence of a scale drum or other similar mechanical means for detecting the amount of a set dose and/or the amount of an injected dose, the injection device can be designed without consideration to the presence, accessibility and/or visibility of such mechanical means. Thus, the injection device may be designed in a manner which provides optimization with regard to other parameters, such as size, shape, user friendliness, etc. This is very advantageous.

The electronic display means may be or comprise an LCD display, an OLED display, an ELD display, a bi-stable e-ink display, or any other suitable kind of display. Using an electronic display reduces the risk that a user misreads a displayed number indicating a set or an injected dose. This is very advantageous, since a misreading may lead to an incorrect dose being injected, and an incorrect dose may have severe consequences to the person receiving the incorrect dose.

The means for electronically detecting the amount of a set dose and/or the means for electronically detecting the amount of an injected dose may be adapted to detect an angular displacement between at least two members, said angular displacement being indicative of the amount of a set dose and/or the amount of an injected dose. In this case one of the members may be rotationally movable during dose setting and/or during injection, while another member remains substantially fixed, e.g. relatively to a housing of the injection device, during the same operation. Alternatively, at least two members may each be rotationally movable, e.g. relatively to a housing of the injection device, either in such a manner that they rotate in the same direction at different angular velocities, or in such a manner that they rotate in opposite directions. In any event, the movement of the members must result in a relative angular displacement, and the angular displacement must be indicative of the amount of a set dose and/or the amount of an injected dose.

The means for electronically detecting the amount of a set dose and/or the means for electronically detecting the amount of an injected dose may comprise at least two substantially disc shaped members being arranged with a substantially fixed mutual distance along a longitudinal direction of the injection device, said substantially disc shaped members being rotationally movable relatively to each other during dose setting and/or injection, and an angular displacement between said substantially disc shaped members may in this case be indicative of the amount of a set dose and/or the amount of an injected dose. According to this embodiment the relative movement between the disc shaped members is purely rotational, i.e. the mutual distance along the longitudinal direction is substantially fixed. The members may, alternatively, have any other suitable shape other than disc shaped.

Alternatively, the mutual distance between the at least two members may be variable during dose setting and/or during injection of a dose.

As an alternative to detecting the amount of a set dose and/or the amount of an injected dose by means of an angular displacement, the amount(s) may be detected by means of a relative linear displacement between two members. Similarly to what is described above, one or both of the members may be linearly movable. It is also conceivable to provide an injection device in which the amount of a set dose is detected by means of a relative rotational displacement, and the amount of an injected dose is detected by means of a relative linear displacement, or vice versa.

The means for electronically detecting the amount of a set dose and/or the means for electronically detecting the amount of an injected dose may be adapted to detect the amount of a set dose and/or the amount of an injected dose by measuring a capacitance. This may advantageously be obtained by providing a set of disc shaped members with a metal coating, thereby forming a set of electrodes when the disc shaped members are positioned opposite each other, and thereby forming a capacitor. By applying the metal to the disc shaped members in a pattern which varies angularly, the area of the resulting capacitor will vary as a function of relative angular displacement between the disc shaped members. Accordingly, since the capacitance, C, is given by $$C = \frac{\varepsilon_0 A}{d},$$

where $\varepsilon_0$ is vacuum permittivity, A is the area of the capacitor, and d is the distance between the electrodes, the capacitance of the capacitor will also vary as a function of the relative angular displacement between the disc shaped members.

Alternatively, the means for electronically detecting the amount of a set dose and/or the means for electronically detecting the amount of an injected dose may be adapted to detect the amount(s) in any other suitable manner, such as optically or inductively, e.g. using quadrature detection. Detection using mechanical switches is also possible.

According to one embodiment, the injection device may comprise means for electronically detecting the amount of a set dose, as well as means for electronically detecting the amount of an injected dose, and the means for electronically detecting the amount of an injected dose may form part of the means for electronically detecting the amount of a set dose. In this case the same detection means is used for detecting the amount of a set dose as well as the amount of an injected dose. This may, e.g., be obtained using a single set of disc shaped members, as described above, being rotationally movable relatively to each other during dose setting as well as during injection of a set dose.

Alternatively, the means for electronically detecting the amount of a set dose and the means for electronically detecting the amount of an injected dose may be separate, e.g. in the form of two sets of disc shaped members, as described above. In this case one set of disc shaped members will be rotationally movable relatively to each other during dose setting, and the other set of disc shaped members will be rotationally movable relatively to each other during injection of a set dose.

As an alternative, the injection device may comprise means for electronically detecting the amount of a set dose only, and the amount of an injected dose may either not be detected or be detected mechanically. Similarly, the injection device may comprise means for detecting the amount of an injected dose only, and the amount of a set dose may be detected mechanically, e.g. using an ordinary scale drum.

The injection device may further comprise a release member for releasing energy stored in the spring member, thereby causing a set dose to be injected. The release member may, e.g., be or comprise a button which the user may press when the desired dose has been set and the injection device has been arranged in such a manner that a dose can be delivered at a selected and suitable injection site. The release member may advantageously be operatively connected to locking means which can maintain the spring member in an energy storing position, e.g. a tensed position, and the operation of the release member should, in this case, cause the locking means to be moved into a position in which it allows the stored energy to be released.

Preferably, the spring member is also arranged to store some amount of energy when no dose is set, i.e. the spring member is preferably pre-tensed to a certain degree. This is in order to ensure that the entire amount of a set dose is actually injected when the injection mechanism is operated.

The spring member may be or comprise a torsion spring. Alternatively, the spring member may be or comprise a compressible spring, a leaf spring, or any other suitable kind of spring being capable of storing and releasing energy. An embodiment comprising a compressible spring will be described in further detail below.

In the case that the spring member comprises a torsion spring, the injection device may further comprise a nut positioned in an interior part of the injection device, said nut being movable during dose setting and during injection between a first position along a longitudinal direction of the injection device, said first position corresponding to a maximum settable dose, and a second position along the longitudinal direction of the injection device, said second position corresponding to complete injection of a previously set dose. According to this embodiment the nut ensures that it is not possible to set a dose which exceeds a maximum dose. The maximum settable dose may, e.g., be chosen so as to ensure that it is safe for the user to inject a set dose, e.g. so as to ensure that there will not be health hazards involved with injecting a set dose. Furthermore, the nut provides an 'end-of-dose' feature, i.e. when the nut is in the second position, the entire dose has been injected, and this may even be communicated to the user, e.g. in a visual, audible and/or tactile manner.

As mentioned above, the spring member may be or comprise a compressible spring, and the compressible spring may extend essentially along the length of the injection device. In this case the injection device preferably has an elongated shape, i.e. the injection device is preferably of a pen-like type. Thereby the direction in which the injection device is elongated defines an axial direction, and the dimension of the injection device along this axial direction defines a length of the injection device. Thus, the compressible spring may extend essentially along this length, i.e. between a proximal end of the injection device and a distal end of the injection device. Accordingly, the compressible spring is relatively long. Thereby it is possible to store a sufficient amount of energy in the spring. Furthermore, the longer the compressible spring is, the smaller a part of its total working range will be used when it is compressed to store energy. This has the consequence that a user will not be able to feel a difference in mechanical resistance from the spring at the beginning of dose setting and at the end of dose setting, and thereby the user will not experience that a spring is being compressed. The compressible spring may be arranged coaxially and surrounding one or more other longitudinal parts of the injection device, e.g. a dose rod and/or a piston rod.

According to one embodiment, the spring member may comprise two or more compressible springs. In this case the spring members may be positioned 'side-by-side', e.g. in parallel with a dose rod and/or a piston rod, thereby providing the possibility of designing the injection device with a relatively flat appearance without reducing the amount of energy it is possible to store in the spring member.

The injection device may further comprise a spring compressing member being movable along a longitudinal direction of the injection device during dose setting and during injection, said spring compressing member being positioned in abutment with the compressible spring, and the spring compressing member may be operatively connected to the dose setting mechanism in such a manner that when the dose setting mechanism is operated the spring compressing member is caused to perform a movement along the longitudinal direction of the injection device, thereby compressing the compressible spring.

Thus, when the dose setting mechanism is operated, the spring compressing member is moved in such a manner that it causes compression of the compressible spring. Thereby energy is stored in the compressible spring. When it is at a later time desired to inject the set dose, the spring compressing member should be allowed to move in an opposite direction, thereby allowing the energy stored in the compressible spring during dose setting to be released. According to one embodiment this may be obtained in the following manner. The spring compressing member is connected to another member via a thread connection. Rotating a dose knob in order to set a dose causes rotation of the spring compressing member, and due to the thread connection, the spring compressing member additionally moves in an axial direction, thereby causing compression of the compressible spring. Furthermore, the spring compressing member should be locked against a reverse movement at this stage, thereby ensuring that the compressible spring remains compressed. When it is desired to inject the set dose, a release mechanism is operated. This causes a lock on the spring compressing member to be released, and the spring compressing member is thereby allowed to move backwards to its initial position in a substantially linear movement, e.g. while causing the piston rod to cooperate with the piston of the cartridge to cause the set dose to be injected.

According to one embodiment the spring compressing member may be adapted to rotationally abut an abutment member when a previously set dose has been injected, said rotational abutment preventing further injection of medication, and the rotational abutment may be obtained by means of a rotational movement of the spring compressing member and/or the abutment member. The rotational abutment provides a very precise indication of when the entire dose has been injected, i.e. a very precise end-of-dose feature. As mentioned above, the rotational abutment may be obtained by allowing rotation of the spring compressing member while the abutment member is kept substantially rotationally fixed, e.g. relatively to a housing of the injection device. Alternatively, the abutment member may be rotated while the spring compressing member is kept substantially rotationally fixed, or the spring compressing member as well as the abutment member may be rotated, preferably towards each other, relatively to a housing of the injection device.

The dose setting mechanism may comprise a dose knob which is rotationally operable, and rotational movement of said dose knob may in this case cause energy to be stored in the spring member. According to this embodiment, the energy is stored in the spring member as a result of a rotational movement of the dose knob. The dose knob is preferably a part of the dose setting mechanism which is manually operable.

According to one embodiment, the means for electronically detecting the amount of a set dose and/or the means for electronically detecting the amount of an injected dose may be adapted to detect movements of a movable member being mechanically biased by a spring force. Thus, the movable member is a part of the injection device which is pre-stressed during setting of a dose. Accordingly, the movements of a pre-stressed member are being monitored for the purpose of electronically detecting the amount of a set dose and/or the amount of an injected dose. This is advantageous because a pre-stressed system tends to have less play than a system which is not pre-stressed, and thereby a more accurate detection can be obtained. In embodiments where the movable member is threadedly associated or engaged with other parts of the dosing mechanism, the pre-stressing of the movable member towards a particular direction of revolution provides for improved rotational sensing of the movable member during dose setting and/or injection.

The movable member is preferably movable in at least two directions, e.g. two opposite angular movements or two opposite translational movements. In this case the spring force preferably acts in one of these directions.

The spring force may be provided by the spring member, and the movable member may, in this case, be connected to the spring member in such a manner that the movable member is caused to move in response to energy being stored in the spring member and/or in response to energy being released from the spring member. In this case the spring force provided by the spring member is used for storing energy to be used during injection, as well as for mechanically biasing the movable member. As an alternative, the spring force may be provided by a separate spring member.

The dose setting mechanism may comprise a click mechanism providing positioning of a dose setting member in discrete steps during dose setting. When a rotatable dose setting member is provided, the setting member is then forced to move in incremental rotational steps, i.e. corresponding to pre-defined dosing steps. In the case that the injection device comprises such a click mechanism as well as a pre-stressed movable member as described above, a very accurate synchronization between the discrete steps and the information presented in the display can be obtained. Accordingly, the information presented in the display, in this case, reflects the actual dose being set in a very accurate manner. This is very advantageous, because it is important that the set dose indicated in the display is the dose which is actually being set, in order to avoid that a wrong dose is injected.

It should be noted, that a similar mechanism could be envisaged for detecting the injected dose.

According to one embodiment, the means for electronically detecting the amount of a set dose and/or the means for electronically detecting the amount of an injected dose may be adapted to detect movements of a movable member, said movable member being connected to the spring member in such a manner that the movable member is caused to move in response to energy being stored in the spring member and/or in response to energy being released from the spring member.

BRIEF DESCRIPTION OF THE DRAWINGS

The invention will now be described in further detail with reference to the accompanying drawings in which FIG. 7 is an exploded view of electronic detection means for use in the injection device of FIGS. 1-6, FIG. 8 is an exploded view of the injection device of FIGS. 1-6.

DETAILED DESCRIPTION OF THE DRAWINGS

Figure 1:
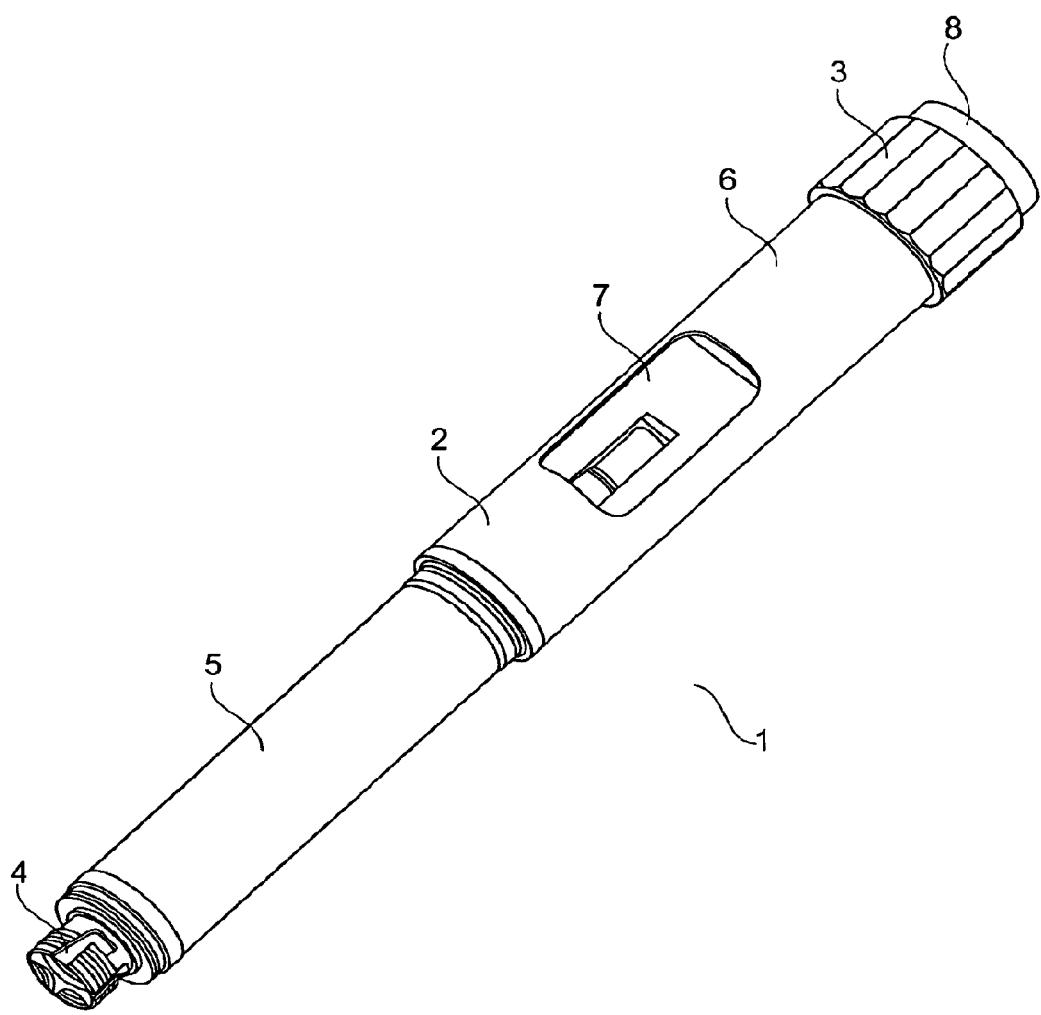
FIG. 1 is a perspective view of an injection device according to a first embodiment of the invention.

FIG. 1 is a perspective view of an injection device 1 according to a first embodiment of the invention. The injection device 1 comprises a housing 2, a dose knob 3 positioned at a proximal end of the injection device 1, and a portion 4 adapted to receiving an injection needle positioned at a distal end of the injection device 1. The housing 2 comprises a cartridge holding portion 5 and a portion 6 being provided with a display 7 for displaying the amount of a set dose and/or the amount of an injected dose. Adjacent to the dose knob 3 an injection button 8 is positioned. When it is desired to inject a dose, the dose knob 3 is rotated in order to set the desired dose, and subsequently, when an injection needle has been positioned at a suitable injection site, the injection button 8 is pressed, thereby causing the set dose to be injected. This will be described further below.

Figure 2:
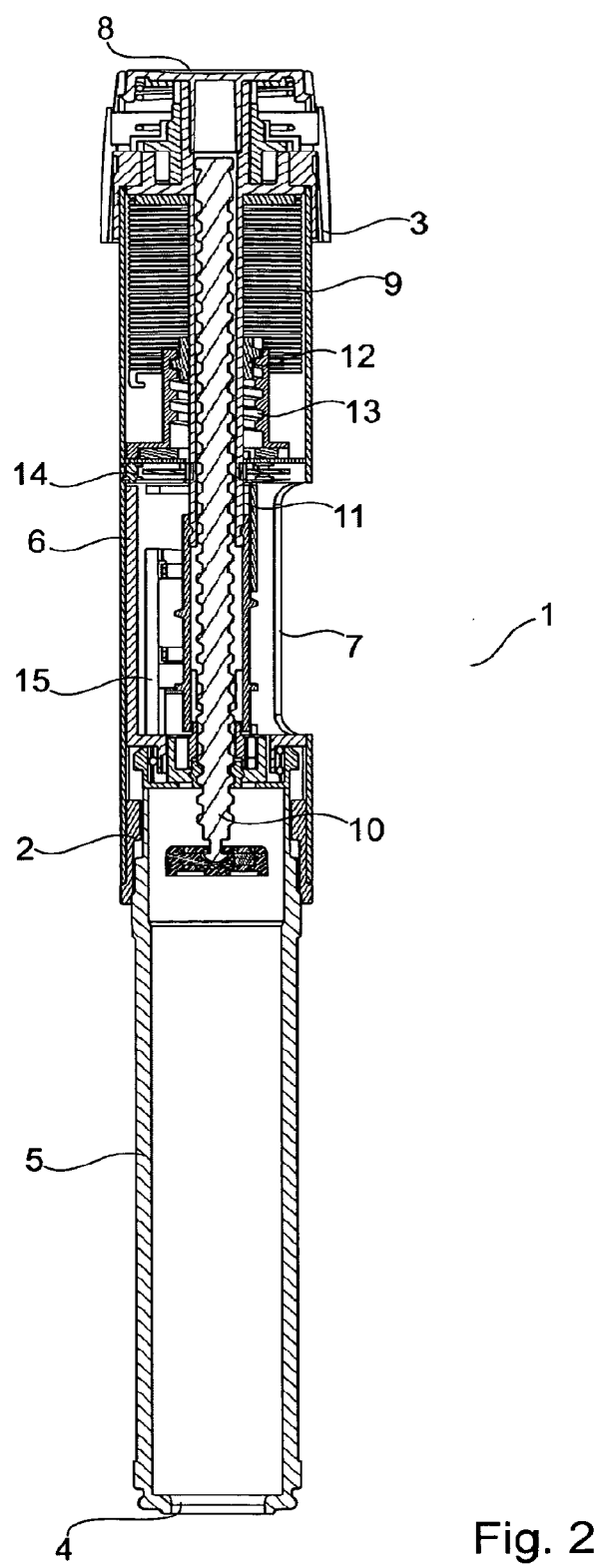
FIG. 2 is a cross sectional view of the injection device of FIG. 1, FIGS. 3-6 are partial views the injection device of FIGS. 1 and 2 at various stages of an injection operation.

FIG. 2 is a cross sectional view of the injection device 1 of FIG. 1. The injection device 1 comprises a torsion spring 9 arranged co-axially with and surrounding a threaded piston rod 10. When the dose knob 3 is rotated during dose setting, the torsion spring 9 is twisted, and energy is thereby stored in the torsion spring 9. This is obtained in the following manner. The dose knob 3 is rotationally coupled to a ratchet 11 during dose setting. The ratchet 11 is also connected to the torsion spring 9. Thus, rotating the dose knob 3 causes the ratchet 11 to rotate, thereby tensioning the torsion spring 9. Furthermore, rotating the dose knob 3 causes nut 12 to travel in a direction towards the dose knob 3 via threaded connection 13. The nut 12 has a function which is similar to the function of a scale drum in injection devices having mechanical detection of the amount of a set dose, i.e. the axial and angular position of the nut 12 indicates the amount of a set dose. However, according to this embodiment of the invention, the nut 12 does not have the function of displaying the set dose, contrary to the function of an ordinary scale drum. It is, therefore, not necessary to position the nut 12 in such a manner that it is readily visible. Accordingly, the nut 12 is positioned as shown in FIG. 2, i.e. in an interior part of the injection device 1.

The injection device 1 is further provided with a set of disc shaped members 14 being adapted to rotate relatively to each other during dose setting as well as during injection. The disc shaped members 14 are each provided with a layer of metal arranged in a pattern, and the disc shaped members 14 thereby form a capacitor having a capacitance which varies as a function of a relative angular displacement between the disc shaped members 14. Thereby the capacitance provides a measure for the angular displacement between the disc shaped members 14, and thereby for the amount of a set or injected dose. This will be described in further detail below.

Electronic circuitry (not shown) is adapted to read the capacitance from the disc shaped members 14 and to communicate a corresponding dose amount to the display 7, thereby causing the relevant dose amount to be displayed to a user.

Linear sensors are furthermore provided for monitoring axial movements of specific parts of the injection device. The linear sensors may be capacitively based sensors of the type generally described in U.S. Pat. No. 5,731,707. During setting of a dose the disc shaped members 14 reflects the angular position of the dose knob 3, and the axial position of one or more of the linear sensors reflects the number of full turns the dose knob 3 has been dialled. Thereby the relative angular position of disc shaped members 14 and the axial position of the linear sensor(s) in combination are used for electronically detecting the set dose, i.e. providing an absolute detection of the dose setting. A similar arrangement could be used for providing an absolute detection of an injected dose.

When it is desired to inject a previously set dose, injection button 8 is pressed, thereby causing the ratchet 11 to be decoupled from the housing 2. Thereby the ratchet 11 is allowed to rotate. The energy stored in the torsion spring 9 during dose setting therefore forces the ratchet 11 to rotate back to its initial position. The ratchet 11 is rotationally coupled to the piston rod 10, via injection ratchet 17 (visible in FIGS. 5, 6 and 8), and the piston rod 10 will therefore also rotate during this. Since the piston rod 10 is threadedly connected to the housing 2, this rotation will cause the piston rod 10 to move in a direction towards the cartridge holding portion 5 of the housing 2. As a consequence, an amount of drug corresponding to the previously set dose will be injected from the injection device 1.

During injection the disc shaped members 14 perform a rotational movement relatively to each other, and the printed circuit 15 reads the corresponding capacitance and causes a corresponding amount of injected dose to be displayed in the display 7, similarly to the situation during dose setting described above.

FIGS. 3-6 are partial views of the injection device 1 of FIGS. 1 and 2 at various stages of an injection operation. For the sake of clarity, parts of the injection device 1 which are not necessary for describing the injection operation have been omitted.

Figure 3:
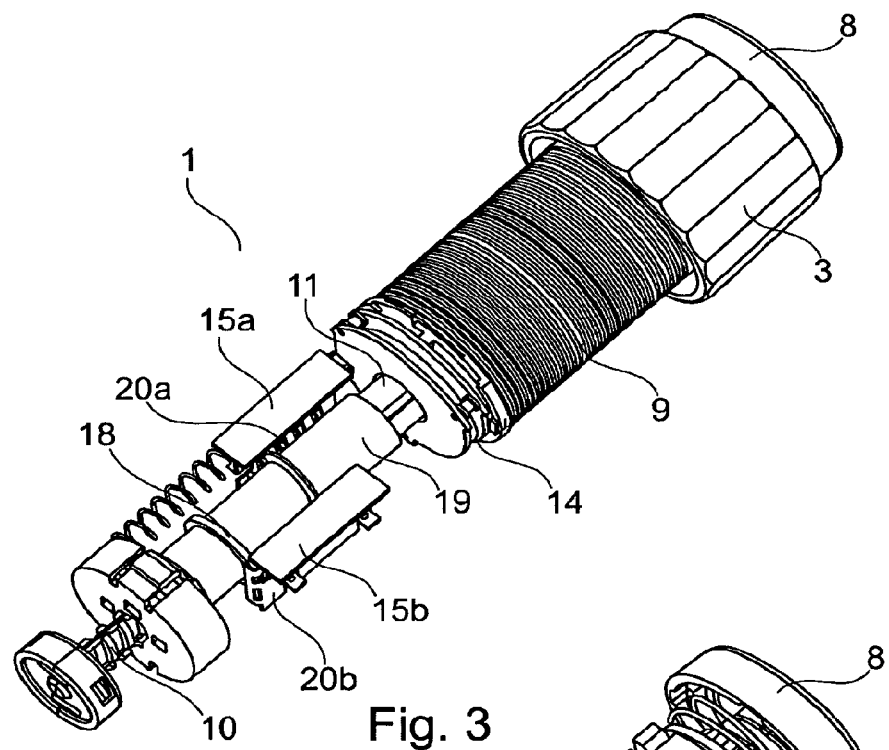

FIG. 3 shows the injection device 1 in an initial position, i.e. the injection device 1 is ready for setting a dose. In order to set the dose, the dose knob 3 is rotated, thereby causing the torsion spring 9 to be tensed, and the disc shaped members 14 to perform a rotational movement relatively to each other, as described above. Furthermore, printed circuit 15*a* is caused to move in a distal direction, i.e. in a direction away from the dose knob 3, due to a connection between track 18 on ratchet extension 19 and track 20*a* arranged on the printed circuit 15*a*.

Figure 4:
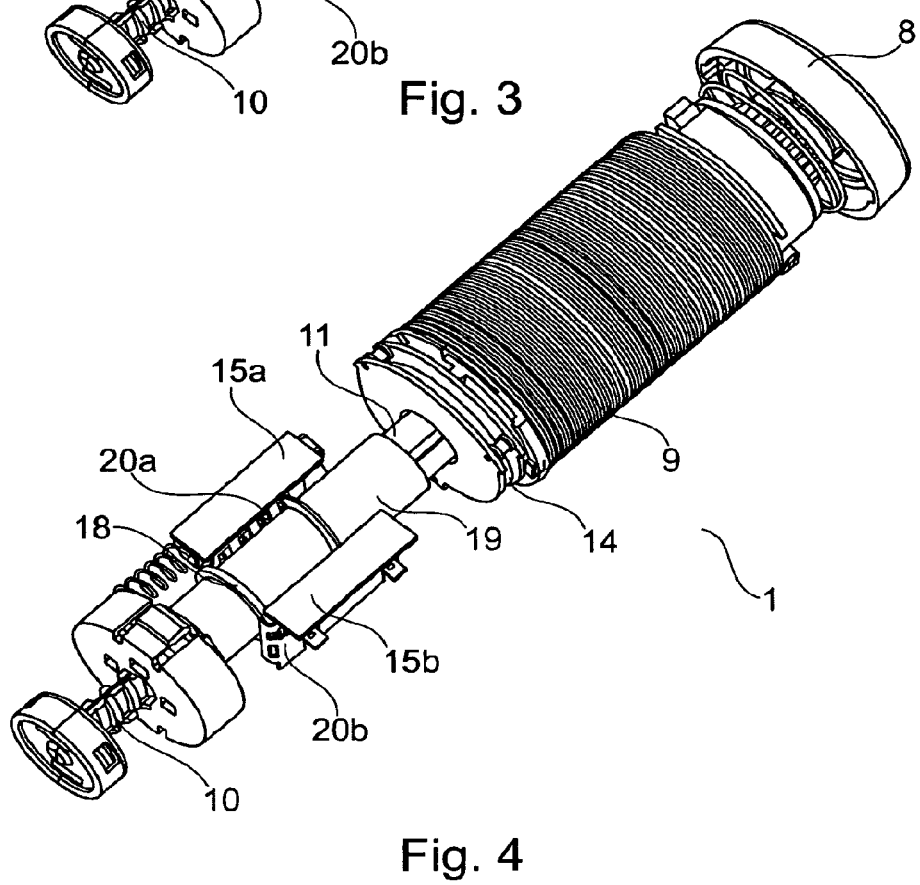

FIG. 4 shows the injection device 1 of FIGS. 1-3 in a position where a dose has been set and the injection device 1 is ready for injection. When comparing FIG. 3 and FIG. 4 it is clear that printed circuit 15*a* has been moved in a distal direction. For the sake of clarity the dose knob is not visible. In order to initiate injection, the injection button 8 is pressed. This causes the ratchet 11 to be decoupled from the housing, thereby causing the energy previously stored in the torsion spring 9 to be released, the released energy rotorically driving the ratchet 11 back. As a consequence the piston rod 10 is moved in a distal direction as described above.

Figure 5:
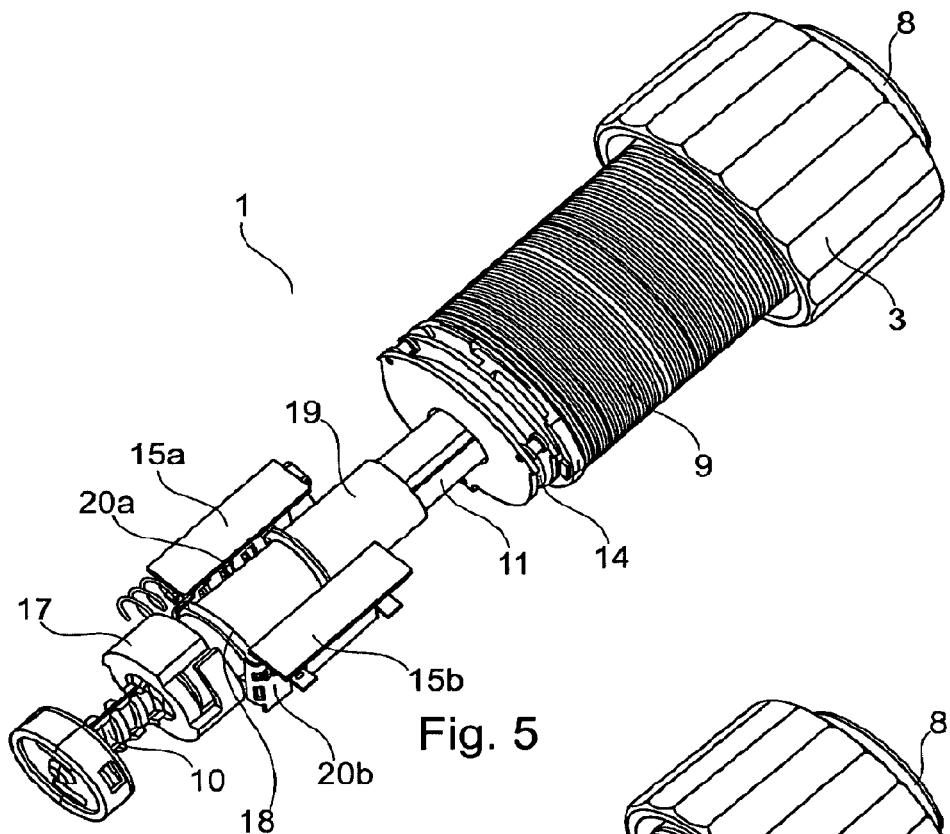

FIG. 5 shows the injection device 1 of FIGS. 1-4 during injection. It is clear from FIG. 5 that ratchet extension 19 has been moved in a distal direction due to operation of the injection button 8.

Figure 6:
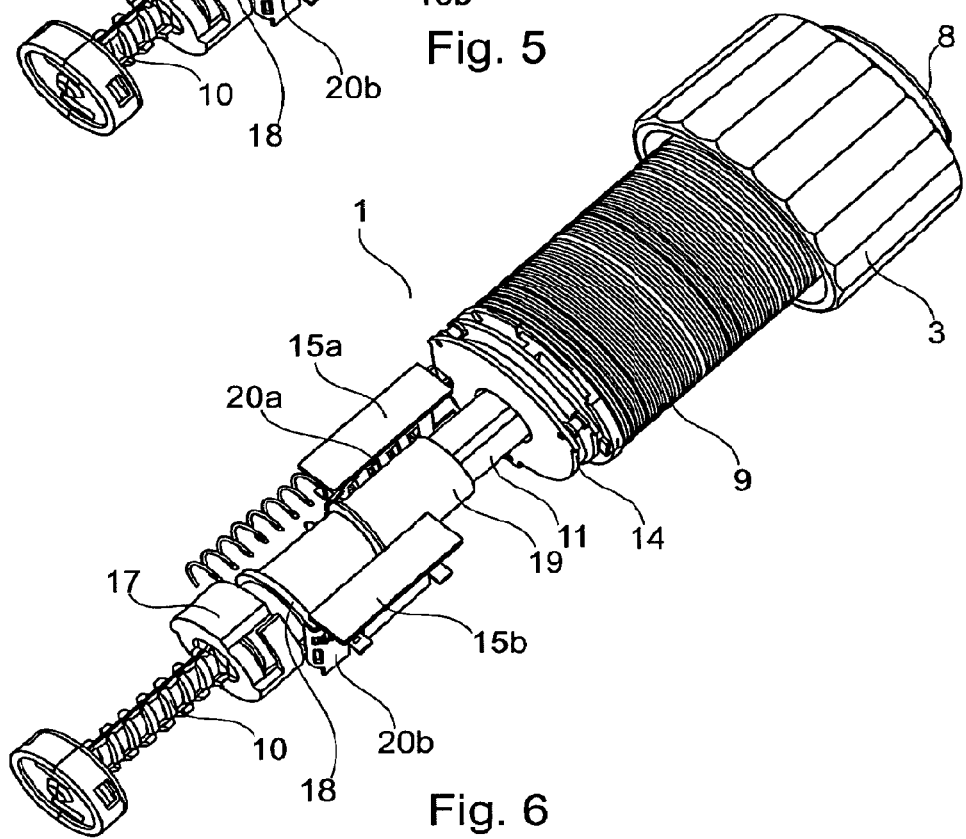

FIG. 6 shows the injection device 1 of FIGS. 1-5 in a position where injection has been completed. Accordingly, printed circuit 15*a* has been moved back to the position of FIG. 3. Comparing FIGS. 3 and 6 it is clear that injection button 8 is still in a pressed-down position in FIG. 6, indicating that the injection has only just been completed, and that the injection device 1 is not yet ready for setting a new dose. Furthermore, it is clear that the piston rod 10 has been moved in a distal direction, indicating that a dose has been injected due to cooperation between the piston rod 10 and a piston positioned in a cartridge containing the drug to be injected.

FIG. 7 is an exploded view of electronic detection means for use in the injection device of FIGS. 1-6, in the form of a set of disc shaped members 14. The electronic detection means comprises two outer discs 21 arranged with a third disc 22 there between. The third disc 22 is provided with a pattern of metal which varies as a function of an angular position of the third disc 22. The outer discs 21 and the third disc 22 are able to rotate relatively to each other. Thereby, the capacitor formed by the third disc 22 and at least one of the outer discs 21 has a capacity which varies as a function of the angular displacement between the outer discs 21 and the third disc 22.

In accordance with this first embodiment, the mechanism ensures that the moveable parts have a repeatable pattern of movement in such a way that zero always represents the same rotational position. The electronical reading can be made absolute, as opposed to a relative reading, thereby ensuring a high security of operation.

FIG. 8 is an exploded view of the injection device 1 of FIGS. 1-6. Thus, FIG. 8 shows the individual parts of the injection device 1 in a clear manner.

Figure 9:
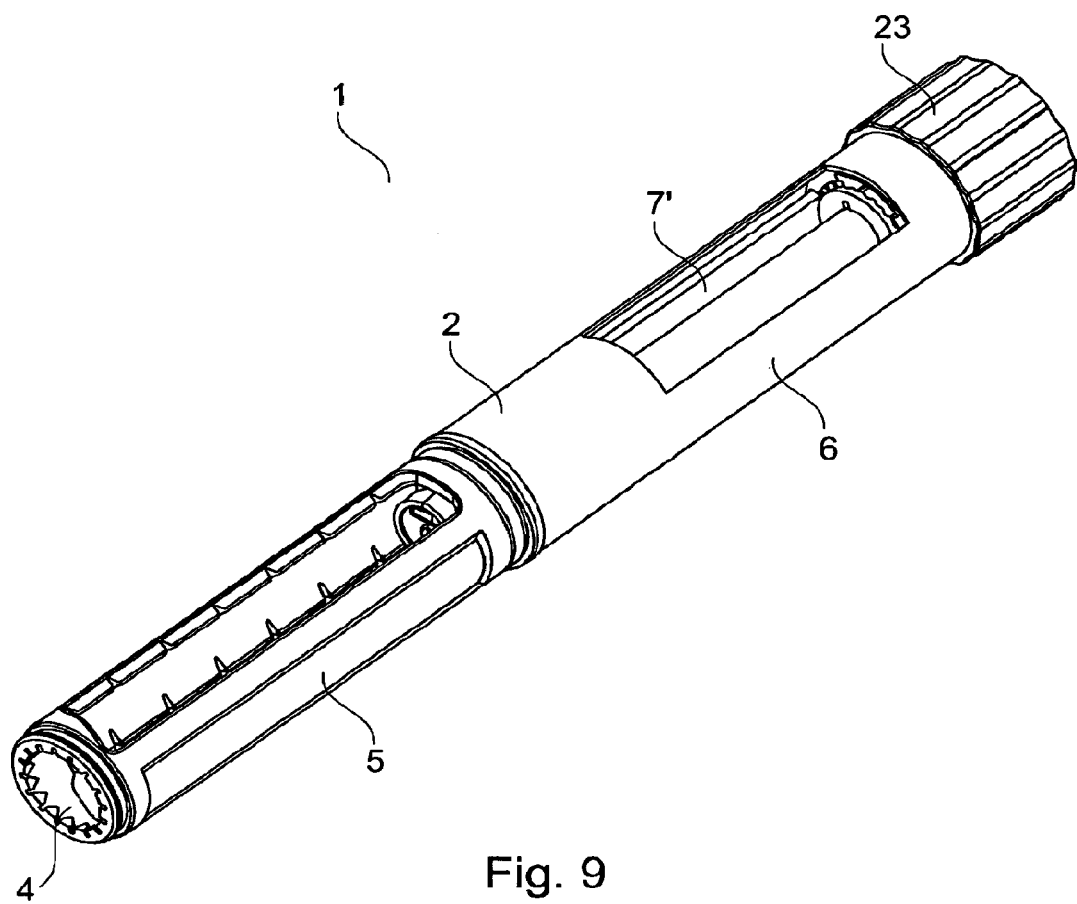
FIG. 9 is a perspective view of an injection device according to a second embodiment of the invention.

FIG. 9 is a perspective view of an injection device 1 according to a second embodiment of the invention. The injection device 1 comprises a housing 2 with a cartridge holding portion 5 and a portion 6 holding a display (not shown) arranged at 7'. At a distal end of the injection device 1 there is a portion 4 for receiving an injection needle. The injection device 1 is further provided with a combined dose knob and injection button 23. Thus the combined button 23 is rotated when it is desired to set a dose, and it is pressed when it is desired to inject a previously set dose.

Figure 10:
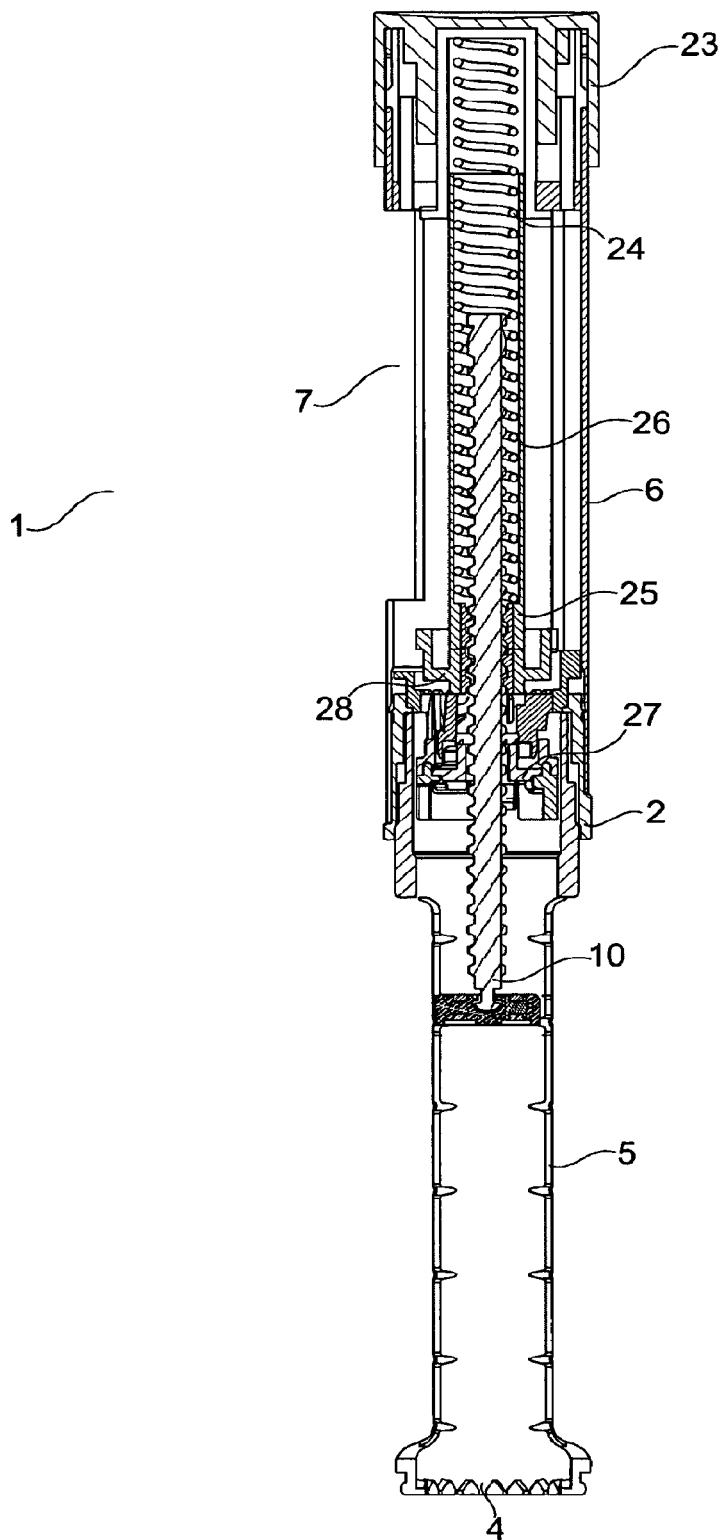
FIG. 10 is a cross sectional view of the injection device of FIG. 9, FIGS. 11-14 are partial views of the injection device of FIGS. 9 and 10 at various stages of an injection operation.

FIG. 10 is a cross sectional view of the injection device 1 of FIG. 9. The injection device 1 according to this embodiment of the invention comprises a compressible spring 24 arranged coaxially with and surrounding a threaded piston rod 10. The compressible spring 24 extends substantially along the entire length of the portion 6 of the housing 2 which holds the display 7.

The injection device 1 further comprises a spring compressing member 25 which is moved in a proximal direction during dose setting, thereby causing the compressible spring 24 to be compressed, thereby storing energy in the compressible spring 24.

When it is desired to set a dose, the combined button 23 is rotated. This causes a dose rod 26 to rotate along. The dose rod 26 is connected to the spring compressing member 25 in such a manner that the spring compressing member 25 is also caused to rotate along with the combined button 23. The spring compressing member 25 is threadedly engaged with the piston rod 10 which, on the other hand, is prevented from rotating due to first locking member 27, and from axial movement due to second locking member 28, also threadedly engaged with the piston rod 10. Accordingly, rotating the spring compressing member 25 results in the spring compressing member 25 moving along the thread of the piston rod 10 in a proximal direction, thereby causing the compressible spring 24 to be compressed.

When it is desired to inject a previously set dose, the combined button 23 is pressed axially in a distal direction. Longitudinal member 30 is moved along, thereby setting the second locking member 28 free to rotate in a manner which will be described in further detail below. Thereby the piston rod 10 is allowed to move axially. The compressed spring 24 will then push the spring compressing member 25 in a distal direction, and the threaded connection between the spring compressing member 25 and the piston rod 10 will cause the piston rod 10 to move in a distal direction, thereby causing the set dose to be injected. When the set dose has been injected, the spring compressing member 25 will enter into abutment with the second locking member 28, the second locking member 28 thereby functioning as an abutment member, thereby preventing that a dose exceeding the set dose is injected.

The injection device according to the shown embodiment is provided with a click mechanism providing audible and/or tactile clicks during rotational operation of the combined button 23 so that each click corresponds to a pre-defined dose increment. Such click mechanism preferably also provides positioning of combined button 23 in discrete operational steps such as 24, 36 or 48 steps per revolution. In the shown embodiment, the click mechanism is provided by a stepped cam surface of combined button 23 which co-operates with a corresponding cam surface which is rotationally fixed with respect to the housing (best seen in FIGS. 11-15). The two opposing cam surfaces are biased towards each other by the compressible spring 24 causing the clicks to be very self indexing and preventing that the system tends to run by it self when resetting a dose.

FIGS. 11-14 are partial views of the injection device 1 of FIGS. 9 and 10 at various stages of an injection operation, i.e. during setting of a dose and injection of the set dose. For the sake of clarity, parts which are not essential for the operation of the injection device 1 have been omitted.

Figure 11:
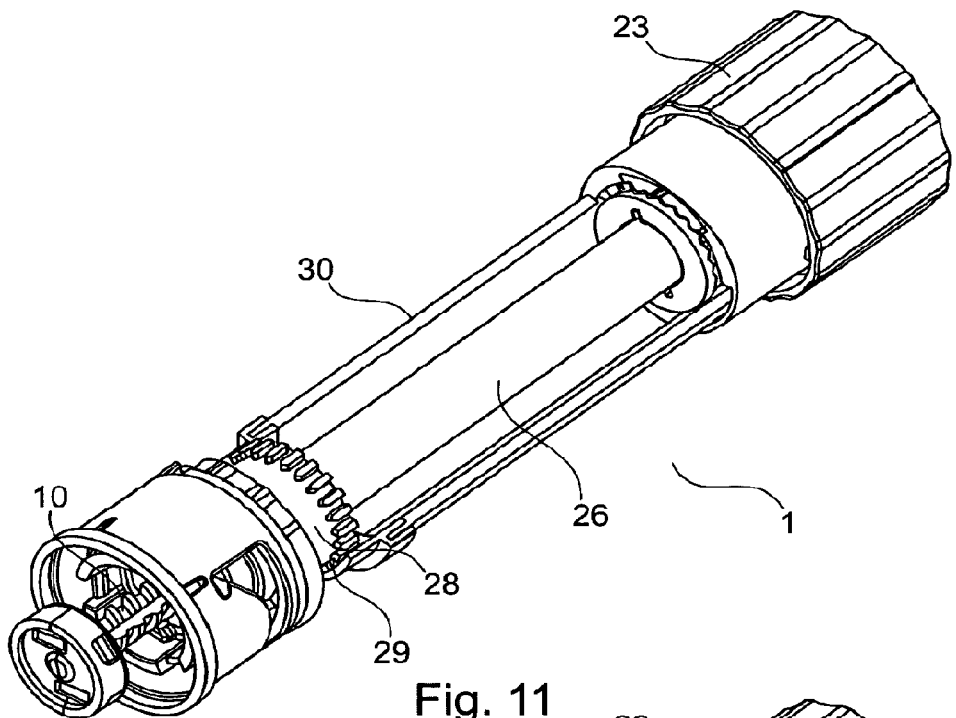

FIG. 11 shows the injection device 1 in a position where it is ready for setting a dose. In order to set a dose, the combined button 23 is rotated as described above, thereby causing the dose rod 26, acting as a spring compressing member, to move in a proximal direction. During dose setting, the second locking member 28 is in engagement with a set of teeth 29 positioned on a longitudinal member 30 which is fixed rotationally to the housing. The second locking member 28 is thereby prevented from rotating relatively to the housing, and the piston rod 10 is thereby prevented from moving axially relatively to the housing.

Figure 12:
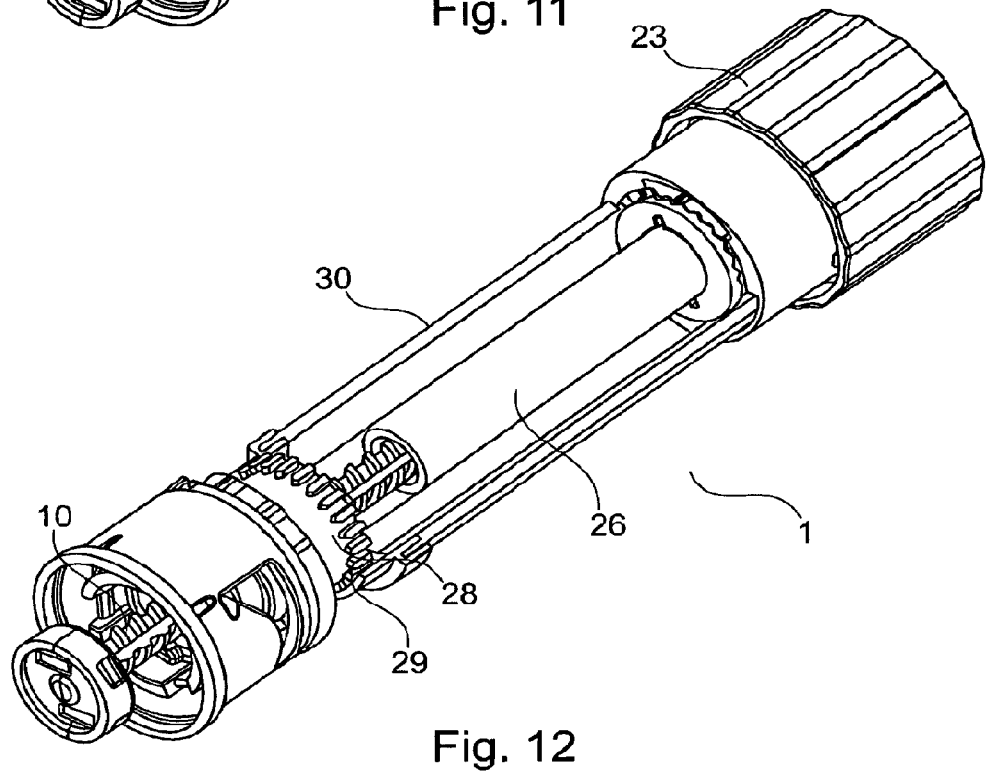

FIG. 12 shows the injection device 1 in a position where a dose has been set and the injection device 1 is ready for injecting the set dose. It is clear from FIG. 12 that the dose rod 26 has been moved in a proximal direction. The second locking member 28 is still in engagement with the set of teeth 29, i.e. the piston rod 10 is still prevented from moving axially relatively to the housing.

In order to cause the set dose to be injected, the combined button 23 is pressed, thereby pushing the longitudinal member 30 in a distal direction. Thereby the set of teeth 29 is moved out of engagement with the second locking member 28. Accordingly, the second locking member 28 will be able to rotate relatively to the housing, and the piston rod 10 will thereby be allowed to move axially relatively to the housing.

Figure 13:
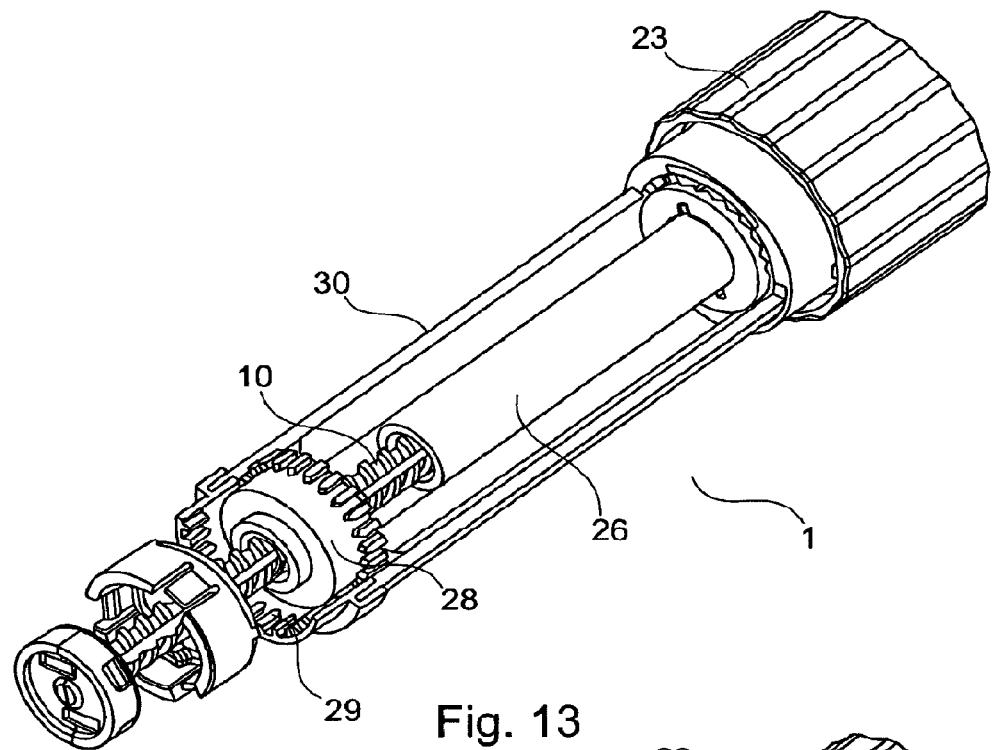

FIG. 13 shows the injection device 1 during injection of a previously set dose. It is clear from FIG. 13 that the second locking member 28 and the set of teeth 29 are not engaging, and that the second locking member 28 is therefore able to rotate relatively to the housing, thereby allowing axial movement of the piston rod 10. Accordingly, the piston rod 10 is able to cause a set dose to be injected.

Figure 14:
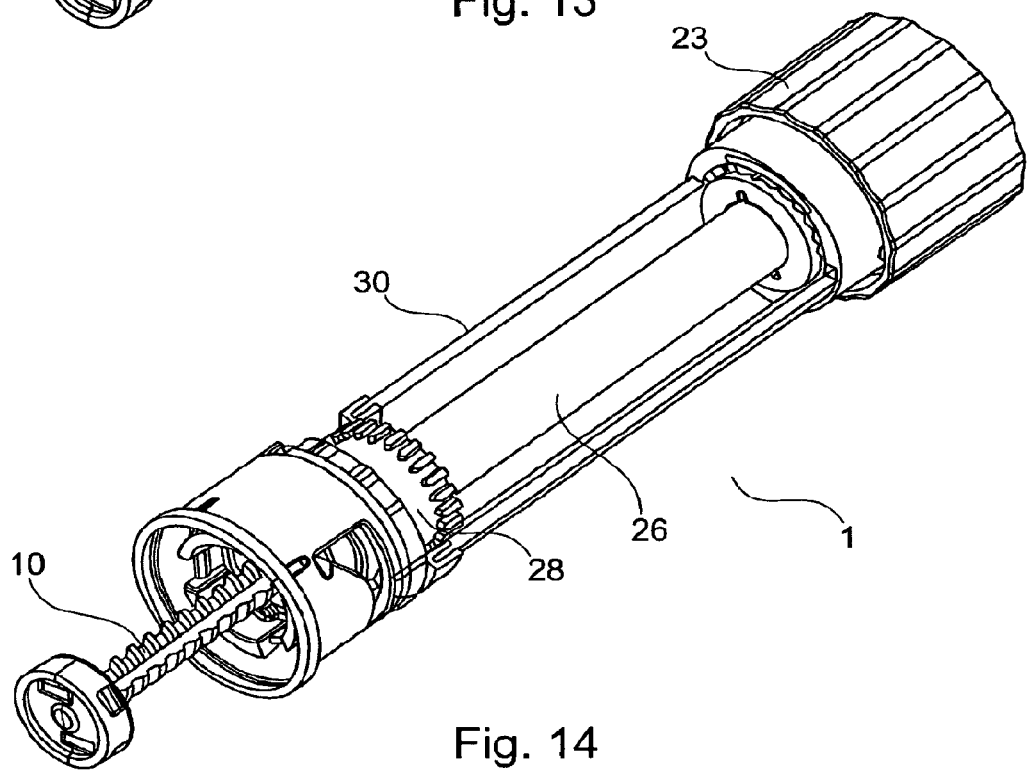

FIG. 14 shows the injection device 1 in a position where injection of a set dose has been completed. Comparing FIG. 11 and FIG. 14 it is clear that the second locking member 28 is not in engagement with the set of teeth (not visible in FIG. 14), and that the injection device 1 is therefore not yet ready for setting a new dose. Furthermore, the piston rod 10 has been moved in a distal direction, indicating that a dose has been injected.

Figure 15:
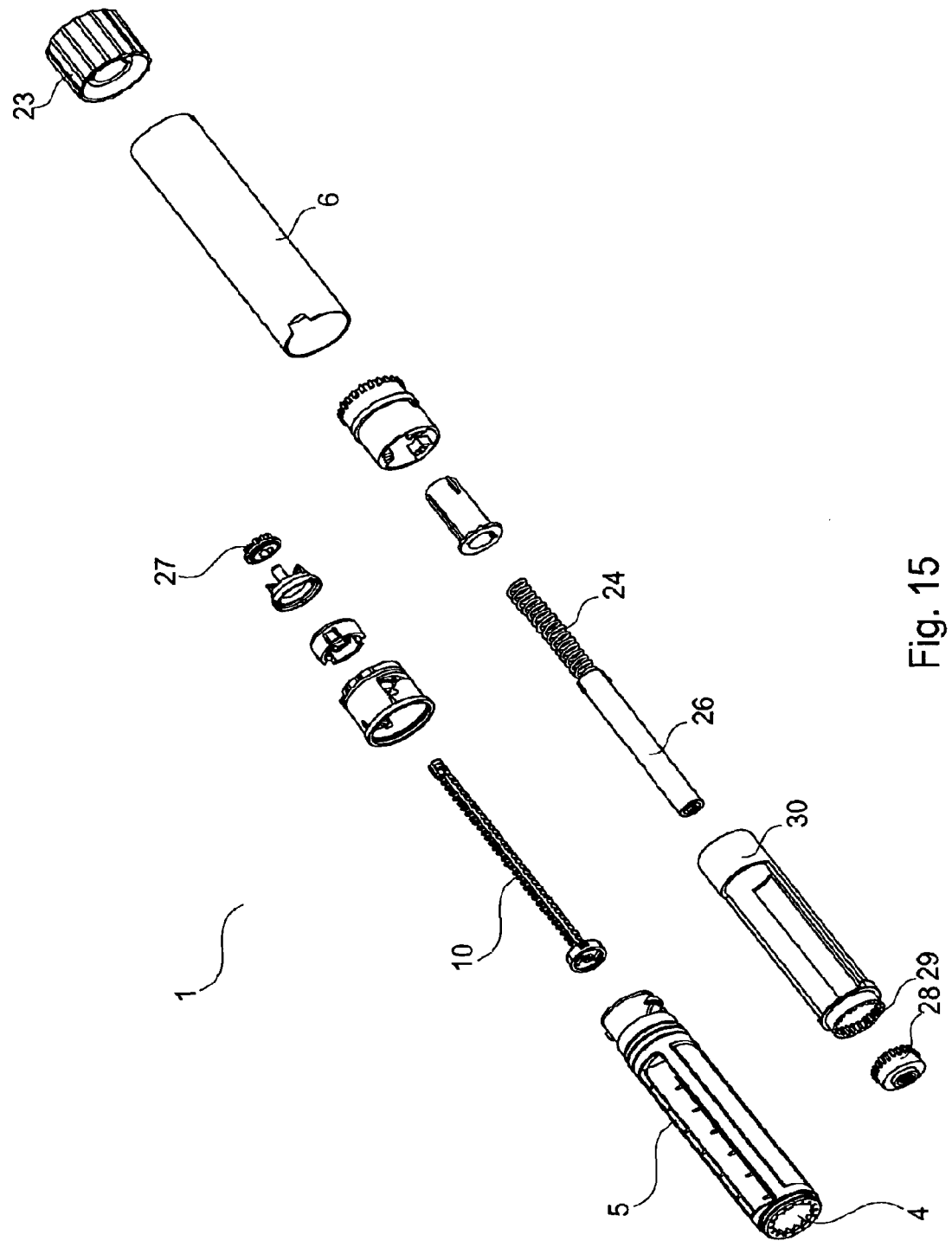
FIG. 15 is an exploded view of the injection device of FIGS. 9-14, FIGS. 16-18 are cross sectional views of an injection device according to a third embodiment of the invention at various stages of an injection operation.

FIG. 15 is an exploded view of the injection device of FIGS. 9-14. Thus, FIG. 15 shows the individual parts of the injection device 1 in a clear manner.

It should be noted that in the embodiment shown in FIGS. 9-15 electronic detection means are not shown. However, it is to be understood that electronic detection means being essentially identical to the ones shown in combination with the embodiment of FIGS. 1-8 could also be envisaged in the embodiment shown in FIGS. 9-15.

FIGS. 16-21 show various illustrations of an injection device 1 according to a third embodiment of the invention. The injection device 1 according to the third embodiment of the invention is operated essentially as the injection device 1 according to the second embodiment which is described above with reference to FIGS. 9-15. Accordingly, the operation of the injection device 1 according to the third embodiment of the invention will not be described in details here.

Figure 16:
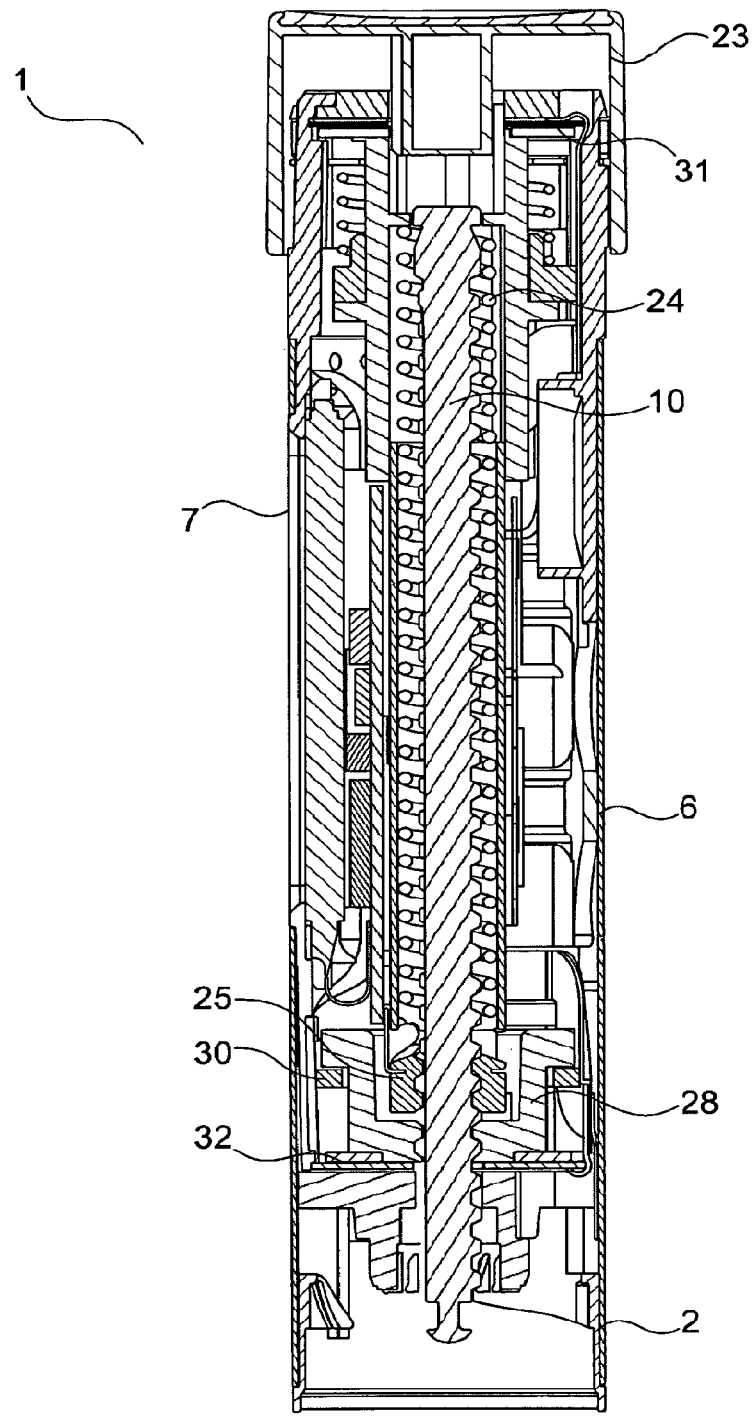

FIG. 16 is a cross sectional view of an injection device 1 according to a third embodiment of the invention. For the sake of clarity, only the portion 6 of the housing 2 which holds the display 7 is shown, the cartridge holding part being omitted. In FIG. 16 the injection device 1 is shown in a position where it is ready for setting a dose.

The injection device 1 is provided with a first set of disc shaped members 31 arranged at a position near the combined button 23. The first set of disc shaped members 31 functions essentially as the set of disc shaped members 14 described above with reference to FIGS. 1-8. Thus, when the combined button 23 is rotated during dose setting the disc shaped members 31 perform relative rotational movements, and thereby the capacitance of the capacitor formed by the disc shaped members 31 varies. Thereby the set dose can be electronically detected. This will be described further below with reference to FIGS. 19-21.

The injection device 1 is further provided with a second set of disc shaped members 32 arranged at a distal position of the portion 6 holding the display 7. The second set of disc shaped members 32 also functions essentially as the disc shaped members 14 described above with reference to FIGS. 1-8. During injection of a previously set dose the piston rod 10 causes the second locking member 28 to rotate. Thereby the discs of the second set of disc shaped members 32 are caused to perform relative rotational movements, and thereby the capacitance of the capacitor formed by the disc shaped members 32 varies. Thereby the injected dose can be electronically detected. This will be described further below with reference to FIGS. 19-21.

Figure 17:
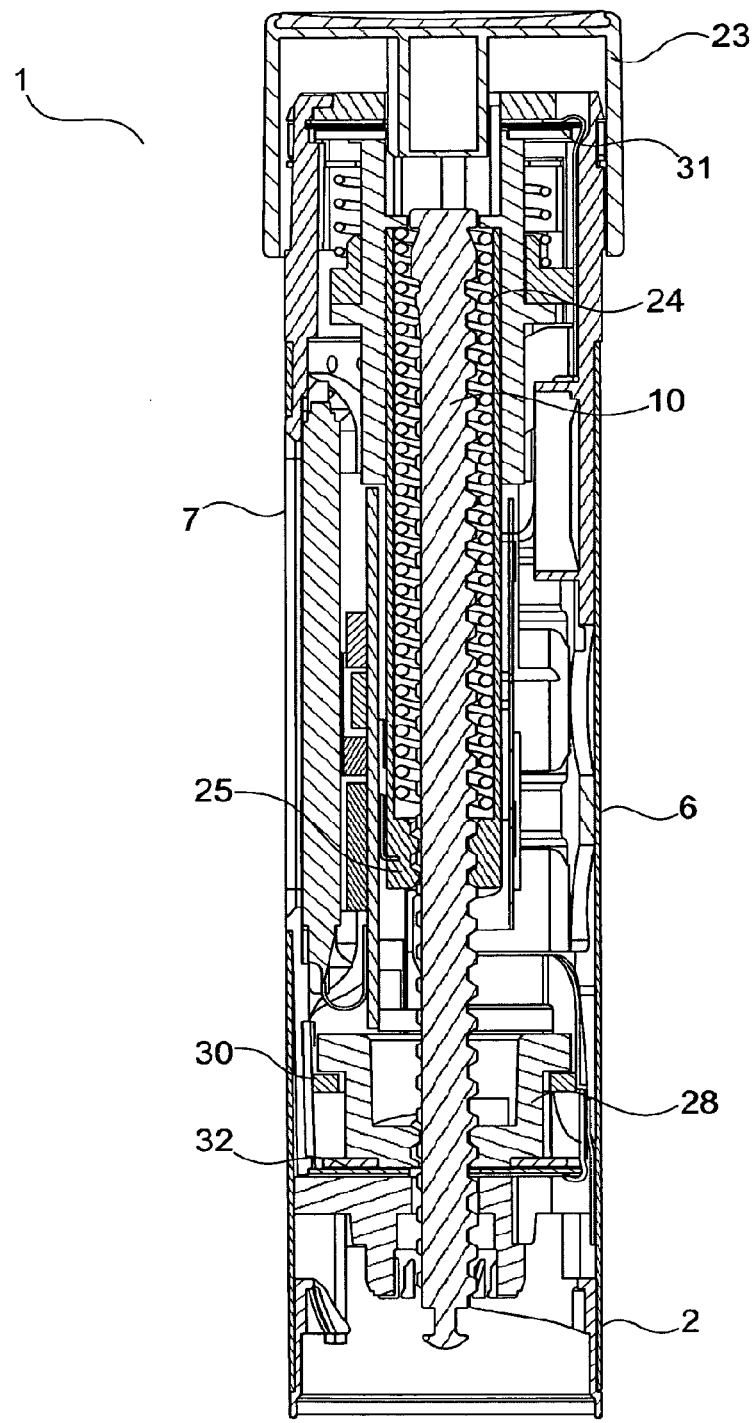

FIG. 17 is a cross sectional view of the injection device 1 of FIG. 16. However, in FIG. 17 a dose has been set, i.e. spring compressing member 25 has been moved in a proximal direction, and thereby compressible spring 24 has been compressed, i.e. energy has been stored in the compressible spring 24.

Figure 18:
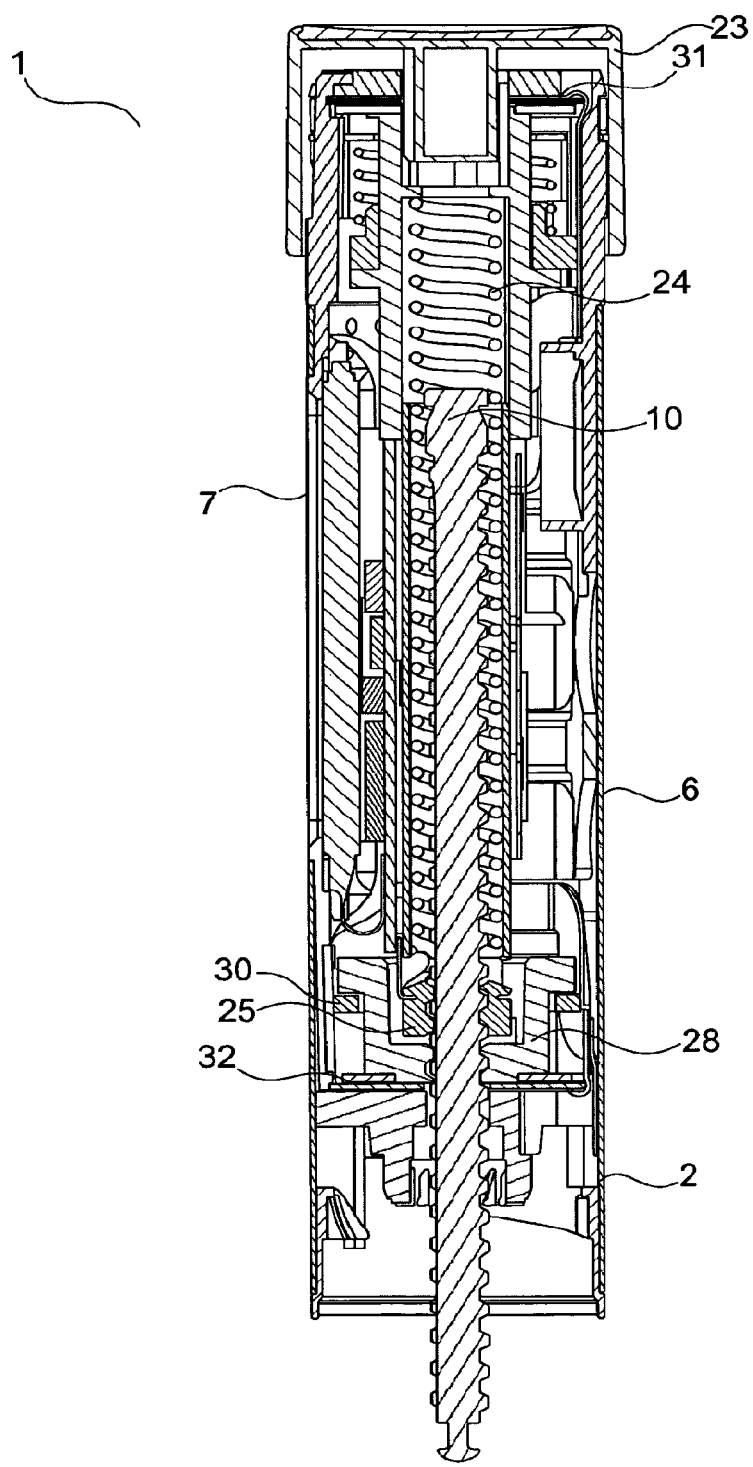

FIG. 18 is a cross sectional view of the injection device 1 of FIGS. 16 and 17. In FIG. 18 the set dose has been injected. It can be seen that the piston rod 10 has been moved in a distal direction as compared to the situation shown in FIG. 16. Delivering of the dose has only just been completed. Thus, the combined button 23 is still in a pressed-down position, thereby keeping the second locking member 28 and the longitudinal member 30 out of engagement, the second locking member 28 thereby being able to perform a rotational movement, allowing the piston rod 10 to move in a distal direction.

Figure 19:
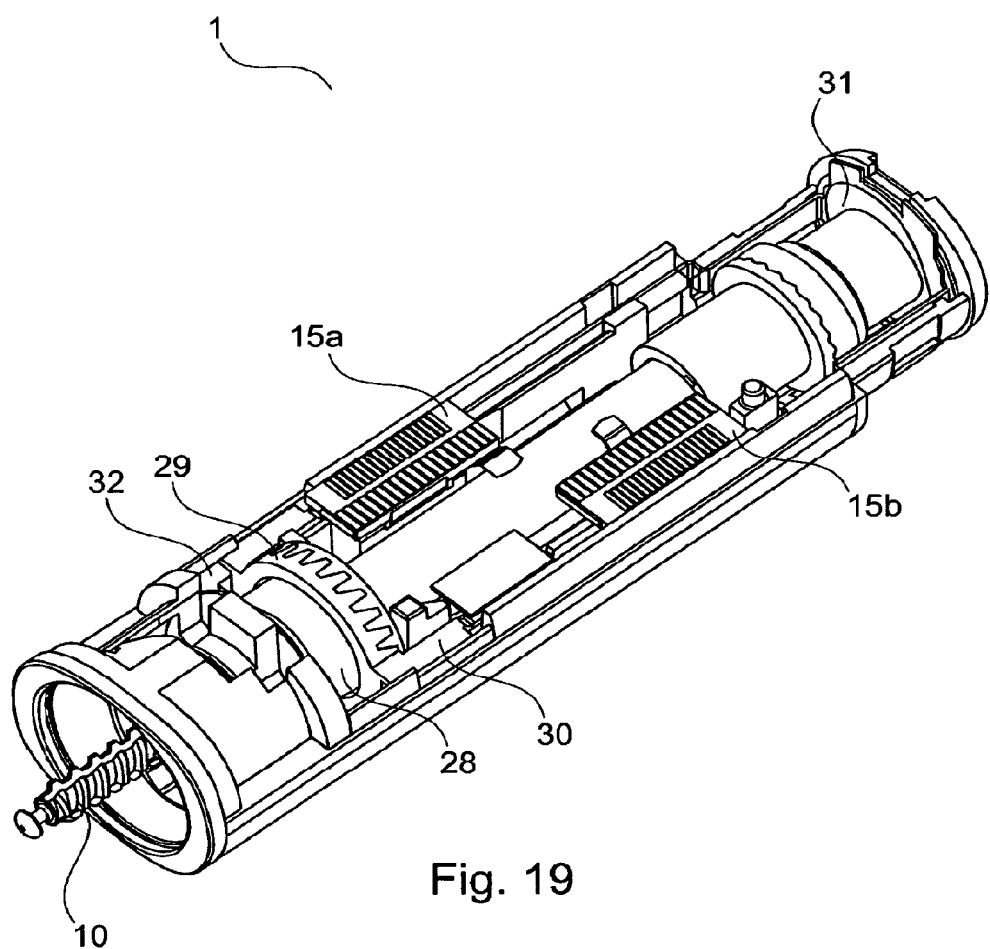
FIGS. 19-21 are partial views of the injection device of FIGS. 16-18 and shown at the same stages of the injection operation.
Figure 20:
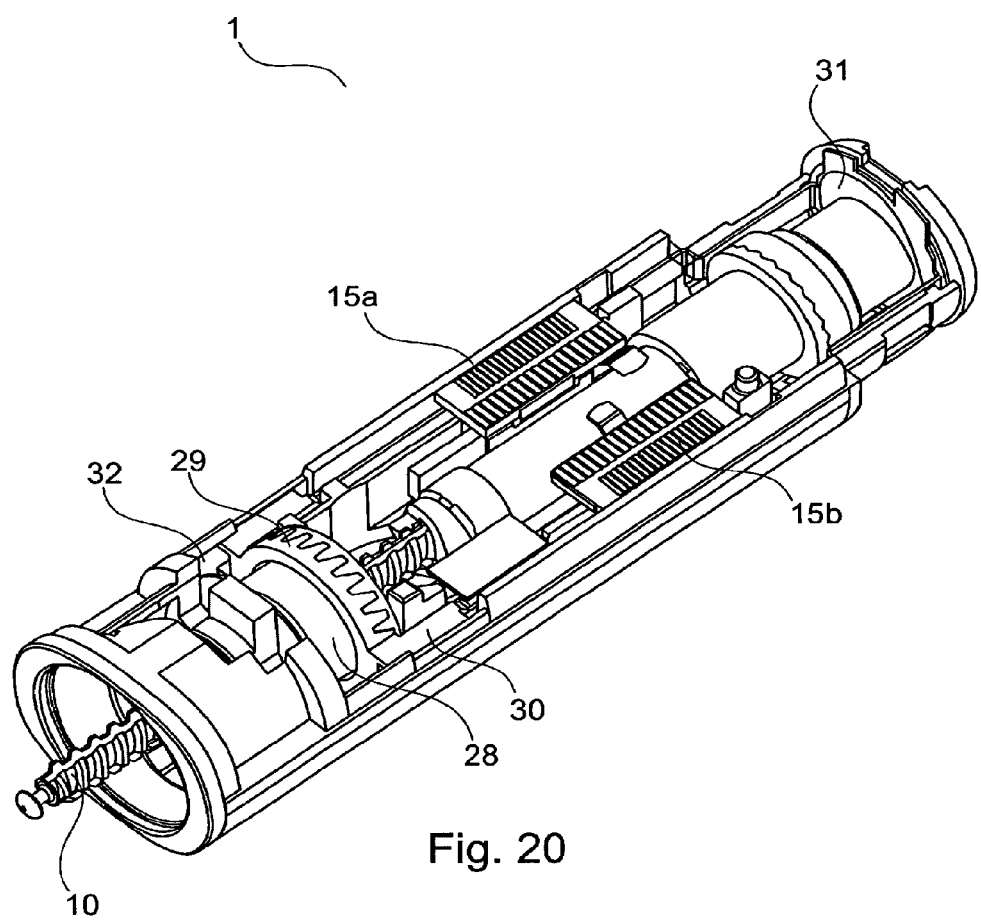
Figure 21:
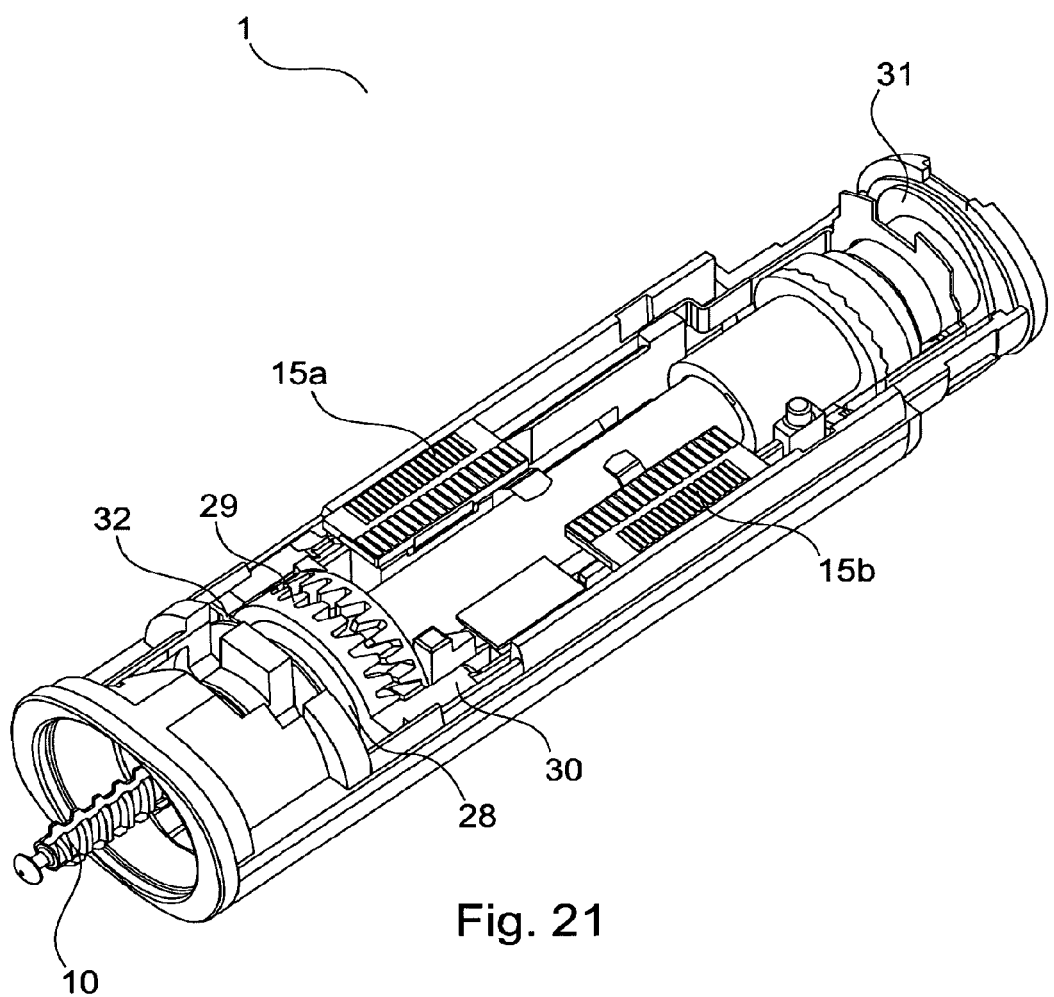

FIGS. 19-21 are partial views of the injection device 1 of FIGS. 16-18 at the stages of an injection operation which are also shown in these Figures. For the sake of clarity, parts which are not essential for the operation of the injection device 1 have been omitted.

FIG. 19 shows the injection device 1 in position where it is ready for setting a dose, i.e. it corresponds to FIG. 16. In FIG. 19 printed circuits 15a and 15b can be seen. During setting of a dose printed circuit 15a moves in a proximal direction in a similar manner to the one described above with reference to FIGS. 1-8. Thereby the set dose is detected electronically in the following manner. The capacitance of the capacitor formed by the first set of disc shaped members 31 reflects the angular position of the combined button 23, and the axial position of the printed circuit 15a reflects the number of full turns the combined button 23 has been dialled. Thereby the relative angular position of the first set of disc shaped members 31 and the axial position of the printed circuit 15a in combination are used for electronically detecting the set dose, i.e. providing an absolute detection of the dose setting.

It should be noted that the set dose could in principle be detected electronically using only the first set of disc shaped members 31, i.e. without the use of printed circuit 15a. Such an embodiment may include an electronic circuitry which electronically monitors the number of complete revolutions that the combined button 23 undertakes during operation thereof, said monitoring being exclusively based upon signals received from the first set of disc shaped members 31. Alternatively, the operation of the dose setting member is limited to 360 degrees operation or less, such that any dose which it may be desired to set can be set within a single turn of the combined button 23. Accordingly, a single unit of a dose would, in this case, correspond to the combined button 23 being rotated through a very small angle, and the first set of disc shaped members 31 would therefore need to be designed in such a manner that such small variations in relative angular position between the discs are detectable.

FIG. 20 shows the injection device 1 in a position where a dose has been set and is ready to be injected. Thus, FIG. 20 corresponds to FIG. 17. It can be seen that the printed circuit 15a has been moved in a proximal direction relatively to the situation shown in FIG. 19.

When it is desired to inject the set dose, the combined button (not shown) is pressed in, and longitudinal member 30 is moved along in a distal direction. Thereby the set of teeth 29 formed on the longitudinal member 30 are moved out of engagement with the corresponding set of teeth formed on the second locking member 28, and the second locking member 28 is allowed to rotate as described above, thereby causing the discs of the second set of disc shaped members 32 to perform relative rotational movements. Furthermore, the printed circuit 15b is caused to move axially in a distal direction. The axial position of the printed circuit 15b provides an indication as to whether the injection device is in dose setting mode or injection mode.

Finally, injection of a set dose causes printed circuit 15a to move in a distal direction, thereby returning to the initial position.

FIG. 21 shows the injection device 1 in a position where a set dose has just been injected. Thus, FIG. 21 corresponds to FIG. 18. It can be seen that the printed circuit 15a has been returned to its initial position, and that the printed circuit 15b has been moved in a distal direction. It can also be seen that the teeth 29 are still out of engagement with the teeth of the second locking member 28.

In accordance with the embodiments described above, the disclosed mechanisms provide space efficient designs of spring assisted injection devices which makes room available for accommodating electronic circuitry such as an electronic display, sensors etc. Particularly, the designs are suitable for injection devices having an electronic display mounted fixedly with respect to the device housing while simultaneously providing reliable routing of the wiring to the various sensor components. In particular, the designs are optimized for spring assisted injection devices where the sensing of rotational parts during both dose setting and injection operations are made feasible.

The invention claimed is:

1. An injection device for injecting a dose of drug, the injection device comprising:
   a housing,
   a dose setting mechanism being operable to set a desired dose, operation of said dose setting mechanism causing energy to be stored in a spring member, the dose setting mechanism defining a first part that rotates during dose setting,
   an injection mechanism comprising a piston rod adapted to cooperate with a piston positioned in a cartridge containing a drug to be delivered in order to cause a set dose to be delivered from the cartridge via the injection device, said injection mechanism being driven by releasing energy previously stored in said spring member during dose setting, the injection mechanism defining a second part that rotates during dose injection,
   means for electronically detecting the amount of a set dose, the means for electronically detecting the amount of a set dose being adapted to detect an angular displacement between the first part and the housing,
   means for electronically detecting the amount of an injected dose, the means for electronically detecting the amount of an injected dose being adapted to detect an angular displacement between the second part and the housing, and
   electronic display means for displaying a set dose and/or an injected dose to a user.

2. An injection device according to claim 1, wherein the means for electronically detecting the amount of a set dose are separate from the means for electronically detecting the amount of an injected dose.

3. An injection device according to claim 1, wherein the means for electronically detecting the amount of a set dose and/or the means for electronically detecting the amount of an injected dose is/are adapted to detect an angular displacement between at least two members, said angular displacement being indicative of the amount of a set dose and/or the amount of an injected dose.

4. An injection device according to claim 3, wherein the means for electronically detecting the amount of a set dose and/or the means for electronically detecting the amount of an injected dose comprise(s) at least two substantially disc shaped members being arranged with a substantially fixed mutual distance along a longitudinal direction of the injection device, said substantially disc shaped members being rotationally movable relatively to each other during dose setting and/or injection, and wherein an angular displacement between said substantially disc shaped members is indicative of the amount of a set dose and/or the amount of an injected dose.

5. An injection device according to claim 1, wherein the means for electronically detecting the amount of a set dose and/or the means for electronically detecting the amount of an injected dose is/are adapted to detect the amount of a set dose and/or the amount of an injected dose by measuring a capacitance.

6. An injection device according to claim 1, wherein the means for electronically detecting the amount of a set dose and/or the means for electronically detecting the amount of an injected dose is/are adapted to detect the amount of a set dose and/or the amount of an injected dose by using mechanical switches.

7. An injection device according to claim 1, further comprising a release member for releasing energy stored in the spring member, thereby causing a set dose to be injected.

8. An injection device according to claim 7, and further comprising locking means adapted to maintain the spring member in an energy storing position, wherein the release member is operatively connected to the locking means so that operation of the release member causes the locking means to be moved into a position allowing the stored energy of the spring member to be released.

9. An injection device according to claim 8, wherein the locking means comprises a rotatable locking member, the rotatable locking member being associated with the piston rod, wherein the rotatable locking member is prevented from rotating relative to the housing during dose setting while being allowed to rotate during dose injection upon operation of the release member.

10. An injection device according to claim 9, wherein the means for electronically detecting the amount of an injected dose is adapted to detect an angular displacement between the rotatable locking member and the housing.

11. An injection device according to claim 7, wherein the spring member is or comprises a torsion spring.

12. An injection device according to claim 11, further comprising a nut positioned in an interior part of the injection device, said nut being movable during dose setting and during injection between a first position along a longitudinal direction of the injection device, said first position corresponding to a maximum settable dose, and a second position along the longitudinal direction of the injection device, said second position corresponding to complete injection of a previously set dose.

13. An injection device according to claim 7, wherein the spring member is or comprises a compressible spring.

14. An injection device according to claim 13, wherein the compressible spring extends essentially along the length of the injection device.

15. An injection device according to claim 13, and further comprising a spring compressing member being movable along a longitudinal direction of the injection device during dose setting and during injection, said spring compressing member being positioned in abutment with the compressible spring, wherein the spring compressing member is operatively connected to the dose setting mechanism in such a manner that when the dose setting mechanism is operated the spring compressing member is caused to perform a movement along the longitudinal direction of the injection device, thereby compressing the compressible spring.

16. An injection device according to claim 15, wherein the spring compressing member is adapted to rotationally abut an abutment member when a previously set dose has been injected, said rotational abutment preventing further injection of medication, wherein the rotational abutment is obtained by means of a rotational movement of the spring compressing member and/or the abutment member.

17. An injection device according to claim 1, wherein the dose setting mechanism comprises a dose knob which is rotationally operable, and wherein rotational movement of said dose knob causes energy to be stored in the spring member.

18. An injection device according to claim 17, wherein the dose setting mechanism comprises a click mechanism providing positioning of the dose knob in discrete steps during dose setting.

19. An injection device according to claim 1, wherein the means for electronically detecting the amount of a set dose and/or the means for electronically detecting the amount of an injected dose is/are adapted to detect movements of a movable member being mechanically biased by a spring force.

20. An injection device according to claim 19, wherein the spring force is provided by the spring member, the movable member being connected to the spring member in such a manner that the movable member is caused to move in response to energy being stored in the spring member and/or in response to energy being released from the spring member.

* * * * *